US010258250B2

(12) United States Patent
Li et al.

(10) Patent No.: US 10,258,250 B2
(45) Date of Patent: Apr. 16, 2019

(54) GPU-BASED PARALLEL ELECTROCARDIOGRAM SIGNAL ANALYSIS METHOD, COMPUTER READABLE STORAGE MEDIUM AND DEVICE

(71) Applicant: SHENZHEN INSTITUTES OF ADVANCED TECHNOLOGY CHINESE ACADEMY OF SCIENCES, Shenzhen, Guangdong (CN)

(72) Inventors: Ye Li, Guangdong (CN); Xiaomao Fan, Guangdong (CN); Furu Xiang, Guangdong (CN); Yunpeng Cai, Guangdong (CN); Fen Miao, Guangdong (CN)

(73) Assignee: SHENZHEN INSTITUTES OF ADVANCED TECHNOLOGY CHINESE ACADEMY OF SCIENCES, Shenzhen, Guangdong (CN)

( * ) Notice: Subject to any disclaimer, the term of this patent is extended or adjusted under 35 U.S.C. 154(b) by 92 days.

(21) Appl. No.: 15/389,978

(22) Filed: Dec. 23, 2016

(65) Prior Publication Data
US 2017/0105643 A1  Apr. 20, 2017

Related U.S. Application Data

(63) Continuation of application No. PCT/CN2015/082040, filed on Jun. 23, 2015.

(51) Int. Cl.
*A61B 5/04* (2006.01)
*A61B 5/0456* (2006.01)
(Continued)

(52) U.S. Cl.
CPC ........ *A61B 5/04017* (2013.01); *A61B 5/0456* (2013.01); *A61B 5/0472* (2013.01); *A61B 5/7203* (2013.01); *A61B 5/7264* (2013.01)

(58) Field of Classification Search
CPC .......................... A61B 5/04017; A61B 5/7203
See application file for complete search history.

(56) References Cited

U.S. PATENT DOCUMENTS

2008/0215807 A1   9/2008  Muraki
2013/0267835 A1  10/2013  Edwards
2015/0305642 A1* 10/2015  Reinke ............... A61B 5/04017
                                                                  600/510

FOREIGN PATENT DOCUMENTS

| CN | 2385674   | 7/2000 |
|----|-----------|--------|
| CN | 1907214   | 2/2007 |
| CN | 102340296 | 2/2012 |
| CN | 102646271 | 8/2012 |
| CN | 103156599 | 6/2013 |

(Continued)

OTHER PUBLICATIONS

First Office Action, issued for corresponding Japanese Patent Application 2016-576010, dated Jan. 16, 2018, 7 pages.

(Continued)

*Primary Examiner* — Joseph M Dietrich
(74) *Attorney, Agent, or Firm* — Hamre, Schumann, Mueller & Larson, P.C.

(57) ABSTRACT

The present disclosure provides a GPU-based parallel electrocardiogram signal analysis method, comprising: performing a filtering process of electrocardiogram signals through a long interval artifact removal and a short interval artifact removal; performing a QRS detection of the filtering-processed electrocardiogram signals through an R-wave position extraction, a QRS complex start and end positions extraction and a QRS complex width extraction; performing (Continued)

an abnormal waveform classification of the QRS-detected electrocardiogram signals through template creation; wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data. By executing one or more steps of the electrocardiogram signal analysis at GPU in parallel, the present disclosure increases the analysis speed of the electrocardiogram signals.

20 Claims, 13 Drawing Sheets

(51) Int. Cl.
*A61B 5/00* (2006.01)
*A61B 5/0472* (2006.01)

(56) References Cited

FOREIGN PATENT DOCUMENTS

| | | |
|---|---|---|
| CN | 103654770 | 3/2014 |
| CN | 104462786 | 3/2015 |
| WO | 2013154855 | 10/2013 |

OTHER PUBLICATIONS

International search Report, issued in the corresponding PCT application No. PCT/CN2015/082040, dated Mar. 31, 2016, 8 pages.
Xu, "The Design of Myocardial Infarction Early Aided Diagnosis System Based on GPU", China Master's Theses Full-Text Database, No. 1, Jan. 15, 2014.
First Office Action and Search Report, issued in the corresponding Chinese Patent Application No. 201580000415.1, dated May 28, 2018, 15 pages.

* cited by examiner

GPU-BASED PARALLEL ELECTROCARDIOGRAM SIGNAL ANALYSIS METHOD, COMPUTER READABLE STORAGE MEDIUM AND DEVICE

This application is a continuation of International Application No. PCT/CN2015/082040, filed on Jun. 23, 2015, which is hereby incorporated by reference in its entirety.

FIELD OF THE INVENTION

The present disclosure relates to the technical field of biomedical engineering, and particularly, to a GPU-based parallel electrocardiogram signal analysis method, computer readable storage medium and device.

BACKGROUND OF THE INVENTION

With the development of the biological information technologies, more and more wearable healthy and medical products can provide personalized healthy and medical services to the people by collecting and analyzing the human electrocardiogram signals, so that a person can acquire his healthy condition without going to any professional medical institutions.

Therefore, the automatic analysis of the electrocardiogram data gradually becomes a research hotspot in the biomedicine field at present. Most of the electrocardiogram data automatic analysis technologies currently are employed for the electrocardiogram data collected in a basic unit of hospital, thus the scale of the electrocardiogram data is very limited. But the service objects of the family health cloud platform are home users in the small, medium and even big cities, and everyday thousands of users upload long-term and short-term electrocardiogram data.

Currently, the health cloud platform adopts a serial electrocardiogram data analysis algorithm, which realizes real-time analysis and real-time feedback of the short-term electrocardiogram data, but the analysis of the long-term electrocardiogram data still costs much time and seriously affects the user's experience. For example, in the current family health cloud platform, the average response time from the upload to the feedback result analysis of the 24 h long-term electrocardiogram data is 35 s, and the consumed time is long.

Related researchers at home and abroad are actively attempting to promote the analysis and processing of the electrocardiogram data from various angles. Although many meaningful research achievements are made in the aspect of electrocardiogram data parallel processing, those research achievements just propose coarse-grained processing procedures for the electrocardiogram data analysis, while the problems occurred at present are still difficult to be solved.

SUMMARY OF THE INVENTION

The present disclosure provides a GPU-based parallel electrocardiogram signal analysis method, computer readable storage medium and device, so as to solve one or more of the above defects.

The present disclosure provides a GPU-based parallel electrocardiogram signal analysis method, comprising: performing a filtering process of electrocardiogram signals through a long interval artifact removal and a short interval artifact removal; performing a QRS detection of the filtering-processed electrocardiogram signals through an R-wave position extraction, a QRS complex start and end positions extraction and a QRS complex width extraction; and performing an abnormal waveform classification of the QRS-detected electrocardiogram signals through template creation; wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data.

In one embodiment, the long interval artifact removal is executed by the multiple threads in parallel, the method comprising: declaring variables at the GPU device side and assigning corresponding global device memory thereto, and copying the electrocardiogram signals from a host memory to a global memory at the GPU device side; segmenting the electrocardiogram signals according to an interval of the long interval artifact removal, calling a kernel function at the GPU device side by each thread, reading a segment of electrocardiogram signals corresponding to the thread from the global memory according to the index number, calculating a standard deviation of the segment of electrocardiogram signals, and storing the standard deviation into a first standard deviation sequence in the global memory according to the index number; removing segments of electrocardiogram signals which go beyond a preset threshold range; calling a reduced summation kernel function at the GPU device side by the thread, and calculating a sum of the standard deviations of all the remained segments of electrocardiogram signals after the removal; calculating a mean value according to the sum, and generating a first threshold range according to the mean value; recalling the kernel function by each thread, reading the standard deviations of the remained segments of electrocardiogram signals after the removal according to the index number and judging whether the standard deviations fall within the first threshold range, and storing judgment results into a first noise sequence in the global memory according to the index number; orderly reading, by each thread, a judgment result and a previous judgment result and a next judgment result adjacent thereto, from the first noise sequence according to the index number; if the previous judgment result and the next judgment result are both that the standard deviation goes beyond the first threshold range, then storing a first flag indicating noise into the first noise sequence according to the index number, otherwise storing a second flag indicating non-noise into the first noise sequence according to the index number, so as to generate a result of the long interval artifact removal; copying the result of the long interval artifact removal from the GPU device side to the host side.

In one embodiment, the number of the threads is $$n = \frac{L}{f*T},$$

and the number of sample points of the electrocardiogram signal correspondingly processed by each thread is f*T, where L is a sample point sequence length of the electrocardiogram signals copied from the host side, f is a sample frequency of the electrocardiogram signals, and T is an interval of the long interval artifact removal.

In one embodiment, the standard deviation is $$M = \sqrt{\frac{\sum_{j=0}^{T*f-1}(p_j - m)^2}{T*f}}, \text{ where } m = \frac{\sum_{j=0}^{T*f-1} p_j}{T*f},$$

where $p_j$ is the electrocardiogram signal at the $j^{th}$ sample point in the segment of electrocardiogram signals, j being an integer and j≥0, f is a sample frequency of the electrocardiogram signals, and T is an interval of the long interval artifact removal.

In one embodiment, an upper limit of the first threshold range is 3 times of the mean value, and a lower limit of the first threshold range is 1/3.5 times of the mean value.

In one embodiment, the preset threshold range is [0.5, 3].

In one embodiment, the short interval artifact removal is executed by the multiple threads in parallel, the method comprising: declaring variables at the GPU device side and assigning corresponding global device memory thereto, and copying the electrocardiogram signals after the long interval artifact removal from a host memory to a global memory at the GPU device side; segmenting the electrocardiogram signals according to an interval $T_1$ of the short interval artifact removal, calling a kernel function at the GPU device side by each thread, reading a segment of electrocardiogram signals according to the index number, calculating a value of equation $$s = \sqrt{\frac{sum}{T_1}},$$

and storing a value of the equation into a second noise sequence in the global memory according to the index number, where sum is a quadratic sum of the electrocardiogram signals in all the segments of electrocardiogram signals; modifying the number of the threads and the number of sample points of the electrocardiogram signals correspondingly processed; recalling the kernel function by each modified thread, reading a flag value in a first noise sequence in a result of the long interval artifact removal uniquely corresponding to the index number of the modified thread, and flagging, through a third flag, a segment of electrocardiogram signals corresponding to the flag value indicating noise; serially screening a segment of electrocardiogram signals corresponding to the flag value indicating noise according to the third flag; calling a reduced summation kernel function at the GPU device side by the modified thread, and calculating a sum of all the remained electrocardiogram signals after the screening; calculating a mean value according to the sum, and generating a second threshold range according to the mean value; re-modifying the number of the threads and the number of the electrocardiogram signals correspondingly processed; recalling the kernel function by the re-modified threads, reading and removing all the values of the equation going beyond the second threshold range from the second noise sequence according to index numbers of the re-modified threads, and generating a result of the short interval artifact removal; copying the result of the short interval artifact removal from the GPU device side to the host side.

In one embodiment, further comprising: the number of sample points of the electrocardiogram signals processed by each thread is $f*T_1$, and the number of the threads is $$n = \frac{L}{f*T_1},$$

where L is a sample point sequence length of the electrocardiogram signals copied from the host side, and f is a sample frequency of the electrocardiogram signals; setting that ThreadsPerBlock threads are corresponding to a thread block, and the number of sample points of the electrocardiogram signals corresponding to each thread block is DataPerBlock=f*T*ThreadsPerBlock, and the number of the thread blocks is BlockNum=(L+DataPerBlock−1)/DataPerBlock.

In one embodiment, further comprising: the number of the modified threads is $$n = \frac{L}{f*T},$$

where L is a sample point sequence length of the electrocardiogram signals copied from the host side, f is a sample frequency of the electrocardiogram signals, and T is an interval of the long interval artifact removal; DataPerBlock1 modified threads are corresponding to a thread block, and the number of the thread blocks is BlockNum1=(L1+DataPerBlock1−1)/DataPerBlock1, where L1 is a length of the first noise sequences of all the results of the long interval artifact removal.

In one embodiment, the method further comprising: the number of the re-modified threads is $$n = \frac{L}{f*T_1},$$

and correspondingly processing one value of the equation by each re-modified thread; setting that ThreadsPerBlock2 re-modified threads are corresponding to a thread block, and the number of the thread blocks is BlockNum2=(n+ThreadsPerBlock2−1)/ThreadsPerBlock2, L is a sample point sequence length of the electrocardiogram signals copied from the host side.

In one embodiment, the R-wave position extraction is executed by the multiple threads in parallel, the method comprising: declaring variables at the GPU device side and assigning corresponding global device memory thereto, and copying the filtering-processed electrocardiogram signals from a memory at a host memory to a global memory at the GPU device side; calling a kernel function by each thread, and reading one to be detected from the filtering-processed electrocardiogram signals according to its index number; performing, by the thread, erosion operations on the read electrocardiogram signal to be detected and its adjacently following w−1 electrocardiogram signals to be detected at different degrees according to a set window size w and a set gradient, and storing a minimum value of the read electrocardiogram signal to be detected and the w−1 electrocardiogram signals to be detected after the erosion operations into a first temporary sequence in the global memory according to the index number, where w is an integer and w≥2; reading, by each thread, one of the minimum values from the first temporary sequence according to the index number; performing dilation operations on the read minimum value and its adjacently following w−1 minimum values at different degrees according to the set window size and the set gradient, and storing a maximum value of the read minimum value and the adjacently following w−1 minimum values after the dilation operations to a second temporary sequence in the global memory according to the index number; reading and calculating differences between the electrocardiogram signals to be detected and the maximum value according to the index number, and storing the differences into a third temporary sequence in the global memory; calling a reduced summation kernel function by the thread to calculate a sum of all the differences in the third temporary sequence; calculating a mean value according to the sum; copying the mean value from the GPU device side to the host side.

In one embodiment, the method further comprising: storing the minimum value of the read electrocardiogram signal to be detected and the w−1 electrocardiogram signals to be detected after the erosion operations into a register; reading the minimum value from the register, and reading the w−1 minimum values from the global memory.

In one embodiment, the set window size is w=5, and the set gradient is k[w]={0, 50, 100, 50, 0}.

In one embodiment, the number of the threads is equal to a sample point sequence length L3 of the electrocardiogram signals copied from the host side; setting that ThreadsPerBlock3 number of threads are corresponding to a thread block, and the number of the thread blocks is BlockNum3= (L3+ThreadsPerBlock3−1)/ThreadsPerBlock3.

In one embodiment, the QRS complex width extraction is executed by the multiple threads in parallel, the method comprising: declaring variables at the GPU device side and assigning corresponding global device memory thereto, and copying a result of the QRS complex start and end positions extraction from a host memory to a global memory at the GPU device side; calling a kernel function at the GPU device side by the thread, reading a start position and an end position in the result of the QRS complex start and end positions extraction according to its index number, calculating a difference between the start position and the end position, storing the difference into the global memory according to the index number, and generating a result of the QRS complex width extraction; copying the result of the QRS complex width extraction from the GPU device side to the host side.

In one embodiment, the start position and the end position of the QRS complex are obtained at the host side according to a method of peak group determination.

In one embodiment, the creation template is executed by the multiple threads in parallel, the method comprising: declaring variables at the GPU device side and assigning corresponding global device memory thereto, and copying a result of the R-wave position extraction from a host memory to a global memory at the GPU device side; calling a kernel function by the thread, reading RR intervals in the result of the R-wave position extraction according to its index number, obtaining an identifier of each RR interval according to a preset criterion, and storing the identifier into the global memory according to the index number to generate a result of the creation template; copying the result of the creation template from the GPU device side to the host side.

In one embodiment, the preset criterion comprises: if an i+1th RR interval RRlist[i+1] adjacent to an ith RR interval RRlist[i] goes beyond a range (0.6*RRlist[i], 1.5*RRlist[i]), an identifier of the RR interval data RRlist[i] is −1, where i is an integer and i≥0; if the RR interval RRlist[i+1] falls within the range (0.6*RRlist[i], 1.5*RRlist[i]) and the RR interval RRlist[i] goes beyond a range (0.8*RRmean, 1.3*RRmean), the identifier of the RR interval RRlist[i] is 0, where RRmean is a mean value of all the RR intervals; and if the RR interval RRlist[i+1] falls within the range (0.6*RRlist[i], 1.5*RRlist[i]) and the RR interval RRlist[i] falls within the range (0.8*RRmean, 1.3*RRmean), the identifier of the RR interval RRlist[i] is 1.

The present disclosure provides a computer readable storage medium containing computer readable instructions which when being executed, cause a processor to at least:

performing a filtering process of electrocardiogram signals through a long interval artifact removal and a short interval artifact removal;

performing a QRS detection of the filtering-processed electrocardiogram signals through an R-wave position extraction, a QRS complex start and end positions extraction and a QRS complex width extraction; and performing an abnormal waveform classification of the QRS-detected electrocardiogram signals through template creation;

wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data.

The present disclosure provides a device, comprising:

a processor; and a memory containing computer readable instructions which when being executed, cause the processor to at least:

performing a filtering process of electrocardiogram signals through a long interval artifact removal and a short interval artifact removal;

performing a QRS detection of the filtering-processed electrocardiogram signals through an R-wave position extraction, a QRS complex start and end positions extraction and a QRS complex width extraction; and performing an abnormal waveform classification of the QRS-detected electrocardiogram signals through template creation;

wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data.

By executing one or more steps of the electrocardiogram signal analysis process at the GUP in parallel, the GPU-based parallel electrocardiogram data analysis method of the embodiment of the present disclosure obviously increases the analysis speed of the electrocardiogram signal.

The GPU-based parallel electrocardiogram data analysis method designed by the present disclosure increases the speed for several and even several tens of times at each phase of the electrocardiogram analysis, and the total time consumption of the electrocardiogram analysis achieves a speed-up ratio of 17 times of the ordinary work station type server. By deploying the parallel algorithm at the GPU server of the family health cloud platform, the requirement of the rapid analysis of large-scale long-term electrocardiogram signal at present can be satisfied.

BRIEF DESCRIPTION OF THE DRAWINGS

In order to more clearly describe the technical solutions in the embodiments of the present disclosure or the prior art, accompanying drawings to be used in the descriptions of the embodiments or the prior art will be briefly introduced as follows. Obviously, the accompanying drawings in the following descriptions just illustrate some embodiments of the present disclosure, and a person skilled in the art can obtain other accompanying drawings from them without paying any creative effort. In the accompanying drawings.

DETAILED DESCRIPTION

To make the objects, technical solutions and advantages of the present disclosure clearer, the embodiments of the present disclosure will be further described in details with reference to the accompanying figures. Herein the exemplary embodiments of the present disclosure and the descriptions thereof are used to explain the present disclosure, rather than limiting the present disclosure.

Figure 1:
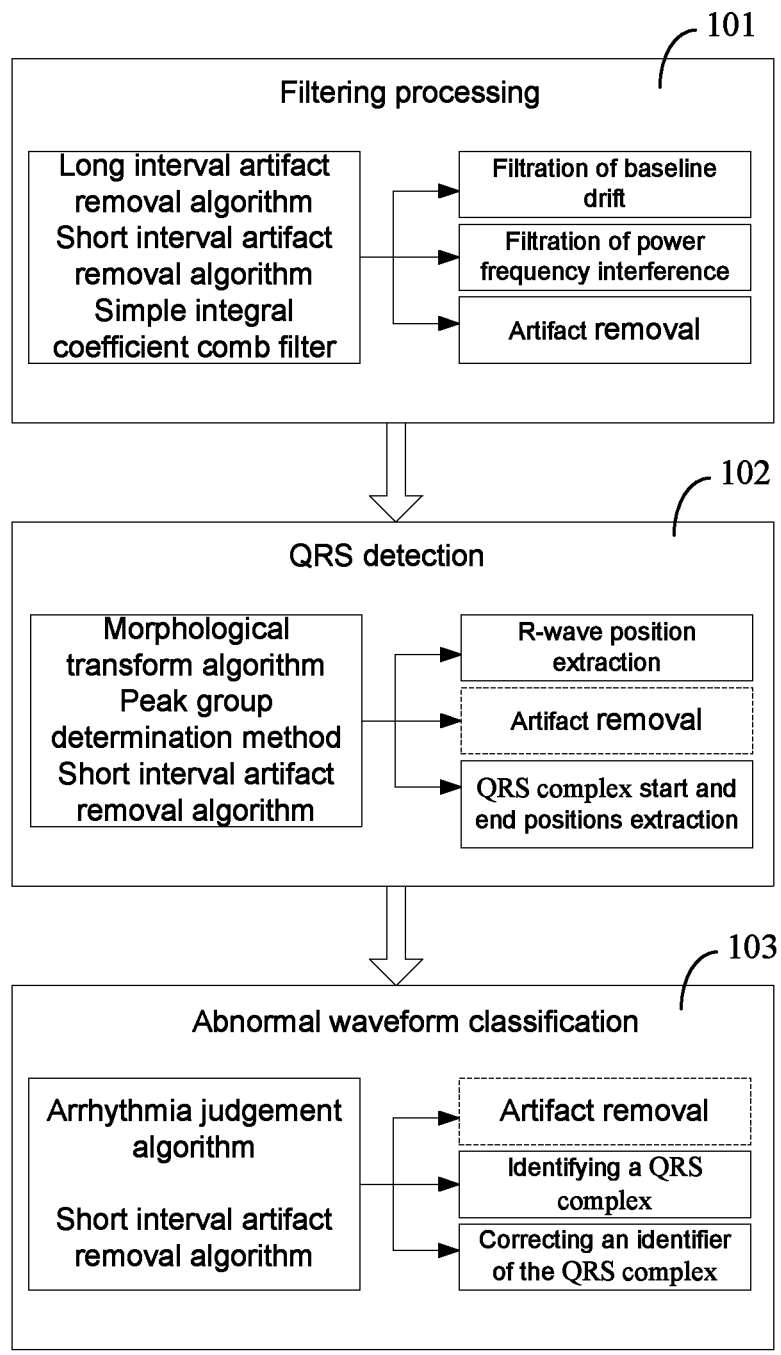
FIG. 1 is a flow diagram of an existed parallel electrocardiogram signal analysis method.

FIG. 1 is a flow diagram of an existed parallel electrocardiogram signal analysis method. As illustrated in FIG. 1, during a filtering process 101, the prior art performs filtering process of electrocardiogram signals using a long interval artifact removal algorithm, a short interval artifact removal algorithm and a simple integral coefficient comb filter, so as to remove artifact interferences including power frequency interference, baseline drift and electromyographical interference, thereby eliminating noise influences generated by the external environment such as human body and signal acquisition instrument. The above three algorithms for the filtering process 101 are all serial algorithms, and the artifact removal is applied in both feature extraction and waveform classification. Thus those three algorithms obviously decrease the processing speed of the electrocardiogram signals.

By analyzing the filtering process including the above three serial algorithms, the inventor finds that each algorithm accounts for ⅓ of the time consumption in the filtering process phase; during data filtering process by the all-pass network simple integral coefficient comb filter, the data is strongly context-dependent, which violates the principle of Single Instruction Multiple Data (SIMD) of parallel calculation under Compute Unified Device Architecture (CUDA) programming model, thus the algorithm is not suitable for parallel execution. When the long interval artifact removal algorithm and short interval artifact removal algorithm are employed during the data filtering process, the data relevance is weak, and the parallel processing is feasible.

Therefore, when the filtering the electrocardiogram signals, the parallel execution of the long interval artifact removal algorithm and/or the short interval artifact removal algorithm can save ⅓ or ⅔ of the time consumption in the filtering process phase.

As illustrated in FIG. 1, in the prior art, two processing in a QRS detection 102, i.e., R-wave position extraction and QRS complex start and end positions extraction, are performed using the serial algorithm. If an algorithm for the parallel execution of R-wave position extraction and QRS complex start and end positions extraction is designed, the electrocardiogram signal analysis speed can be further improved.

Still as illustrated in FIG. 1, in the prior art, an abnormal waveform classification 103 is performed by identifying the QRS complex through a serial algorithm. If a parallel algorithm is designed to identify the QRS complex, a faster electrocardiogram signal analysis speed can be obtained.

Figure 2:
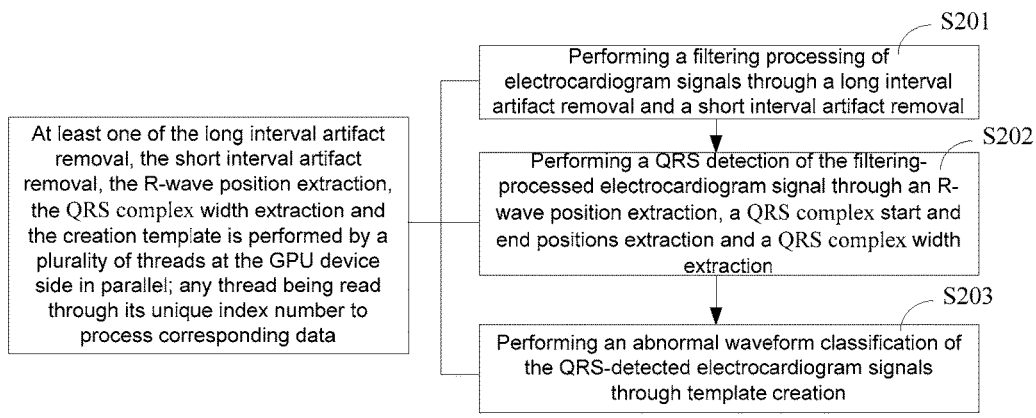
FIG. 2 is a GPU-based parallel electrocardiogram signal analysis method provided by an embodiment of the present disclosure.

In order to solve the problems existed in the prior art, an embodiment of the present disclosure provides a GPU-based parallel electrocardiogram signal analysis method. As illustrated in FIG. 2, the parallel electrocardiogram signal analysis method provided by the embodiment of the present disclosure comprises the steps of:

S201: performing a filtering process of electrocardiogram signals through a long interval artifact removal and a short interval artifact removal.

S202: performing a QRS detection of the filtering-processed electrocardiogram signal through an R-wave position extraction, a QRS complex start and end positions extraction and a QRS complex width extraction.

S203: performing an abnormal waveform classification of the QRS-detected electrocardiogram signals through template creation.

Wherein, at least one of the long interval artifact removal, the short interval artifact removal, the R-wave position extraction, the QRS complex width extraction and the template creation is parallel performed by a multiple threads at the GPU device side in parallel; any thread being read through its unique index number to process corresponding data.

By executing in parallel, at the GPU, at least one of the long interval artifact removal algorithm, the short interval artifact removal algorithm, the R-wave position extraction, the QRS complex width extraction and the creation template, the parallel electrocardiogram signal analysis method provided by the embodiment of the present disclosure improves the electrocardiogram signal analysis speed to some extent.

In one embodiment, the long interval artifact removal may be executed with a serial algorithm. During the long interval artifact removal, a noise sequence noiselist[length] will be generated with an array length as follows:

length=ecgnum+T, where, ecgnum denotes the array length of the original electrocardiogram signal; T denotes the interval of the long interval artifact removal; if a certain segment of data is judged as noises, 1 is written to corresponding position of the noise sequence, otherwise 0 is written.

Figure 3:
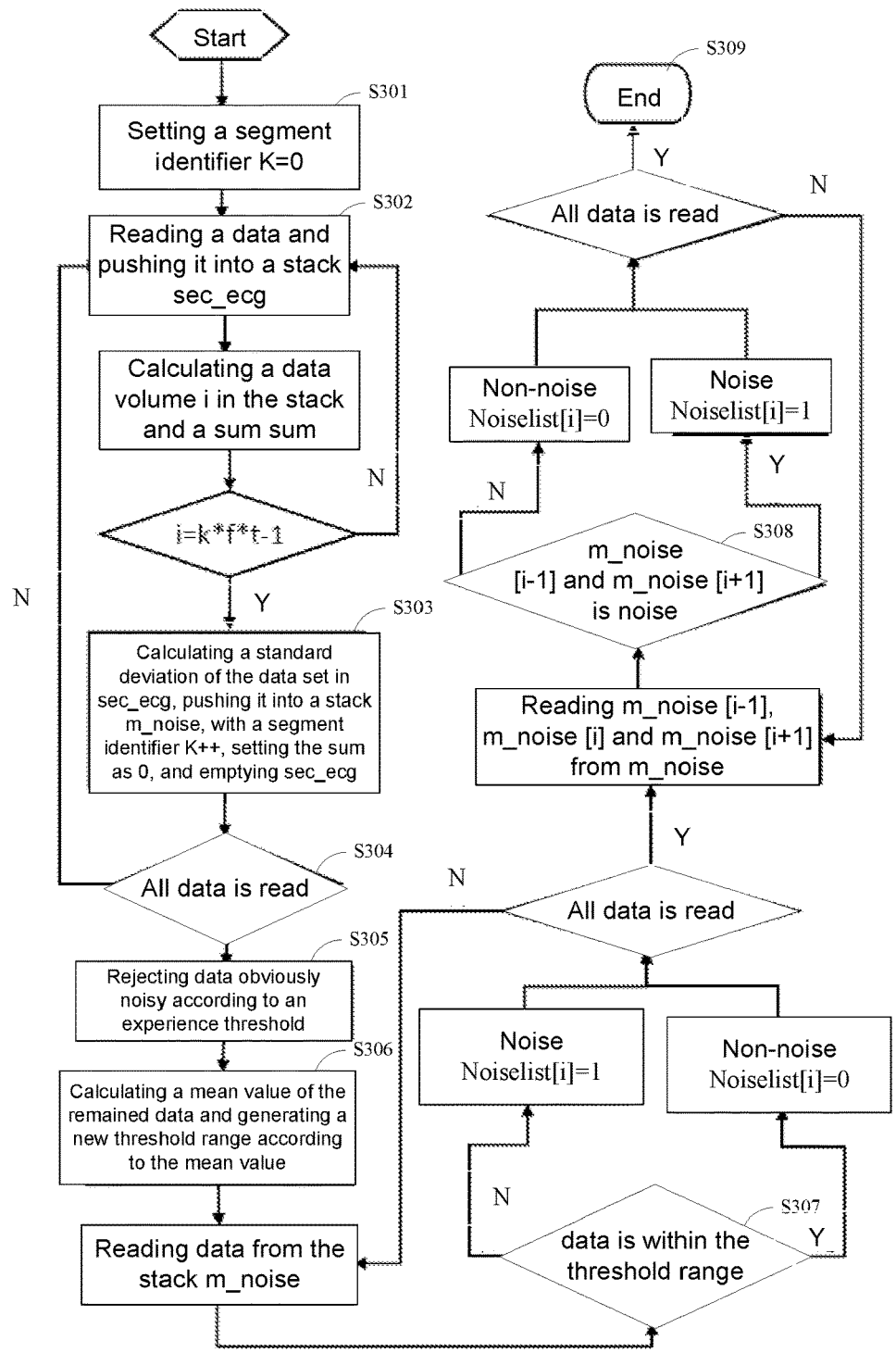
FIG. 3 is a flow diagram of a serial execution algorithm of long interval artifact removal provided by an embodiment of the present disclosure.

FIG. 3 is a flow diagram of a serial execution algorithm of long interval artifact removal provided by an embodiment of the present disclosure. As illustrated in FIG. 3, the serial execution algorithm of long interval artifact removal comprises the steps of:

S301: initializing a segment identifier of electrocardiogram signals as K=0.

S302: orderly reading electrocardiogram signal from original electrocardiogram signals.

S303: when f*T points of electrocardiogram signal are read, calculating a standard deviation of each segment of electrocardiogram signal set according to a standard deviation equation M, and adding the segment identifier K by 1:

$$M = \sqrt{\frac{\sum_{j=0}^{T*f-1}(p_j-m)^2}{T*f}}, m = \frac{\sum_{j=0}^{T*f-1} p_j}{T*f},$$

where f is the sample frequency of the electrocardiogram signals, $p_j$ denotes the jth point of sample data in each segment of electrocardiogram signal set, and j is a positive integer, i.e., j≥0.

S304: repeating steps S302 and S303, until all the electrocardiogram signal is processed.

S305: judging whether the standard deviation of each segment of electrocardiogram signal set falls within an experience threshold range [0.5, 30], and calculating a mean value of the standard deviations of the electrocardiogram signal sets within the experience threshold range.

S306: calculating upper limit temp_h and lower limit temp_1 of the new threshold according to the mean value temp_M to obtain a new threshold range, where, temp_h=temp_M*3, temp_1=temp_M+3.5, temp_1≥0.6.

S307: making a judgment for an electrocardiogram signal noise segment according to the new threshold range obtained in step S306, i.e., if a segment of electrocardiogram signal set has its standard deviation falling within the new threshold range, it is not a noise segment and denoted as noiselist[i]=0, otherwise it is a noise segment and denoted as noiselist[i]=1.

S308: retraversing, and if two segments of electrocardiogram signal before and after a certain segment of electrocardiogram signal are both noise segments, judging the segment of electrocardiogram signal as a noise segment.

S309: ending the long interval artifact removal.

By analyzing the serial algorithm of the long interval artifact removal, the inventor finds that there are four loop bodies in the long interval artifact judging procedure, while in the CUDA structure, threads are organized in the manner of single instruction multiple data, thus the loop bodies are suitable for a parallelization improvement.

The numbers of thread blocks and thread resources therein are specified when a kernel function is called. The number of thread blocks (BlockNum) can be calculated from the length of the original electrocardiogram data and the given number of threads in each thread block (ThreadsPerBlock) according to equations (1) and (2):

DataPerBlo ck=f*T*ThreadsPer Block  (1)

BlockNum=(ecgnum+DataPerBlo ck−1)/DataPerBlo ck  (2)

During the long interval artifact judgment, the first loop is a nested loop realizing a function of calculating the standard deviation of each data subset of the entire data set according to the number of data subsets specified by the inner loop. By performing a parallelization improvement of the loop based on the characteristics thereof, one thread can calculate the standard deviation of one data subset, and a multiple threads can be executed in parallel simultaneously time without any communication.

The second loop realizes a function of removing a part of the data according to the experience threshold, and calculating a mean value of the remained data. A parallelization improvement of the loop may be made in a manner of CPU serial execution to generate a new array, and then a kernel function of reduced summation is called to calculate a sum of data in the new array.

The third loop realizes a function of judging whether a data set corresponding to a result set m_noise generated by the first loop is noise. The specific process is to read a value from the result set m_noise each time, and compare the value with the experience threshold to judge whether data corresponding to the value is noise. In that case, by making a parallelization improvement of the loop, a length number of threads can be started and each thread only corresponds to one value in the result set m_noise, so that each thread reads a corresponding value from m_noise according to an index number thereof. Next, the value read according to the index number of the thread is compared with a set threshold, and a comparison result is written into an array noiselist according to the index number of the thread.

The fourth loop reconfirms the noise sequence generated by the third loop. This loop is based on a judgment criterion that "if two data sets before and after a data subset are both judged as noises, the segment of data set is also noise". During realization of the function, a data value is read from the array noiselist each time, then two data values adjacently before and after the data value are read, and the data value is modified according to the above judgment criterion. By making a parallelization improvement of the loop, a length number of threads can be started and the index number of each thread only corresponds to one value in the array noiselist, so that each thread reads a corresponding value and values adjacently before and after the value from the array m_noise according to the index number thereof. Next, corresponding calculation can be performed according to the read values.

Since the improved fourth loop is executed in parallel, it shall be considered whether the read values adjacently before and after the value are heart data.

For the convenience of analysis, the value corresponding to the index number of the thread may be denoted as a, the values adjacently before and after a may be denoted as font and back, respectively, a value adjacently before font may be denoted as b, and a value adjacently after back is denoted as c. According to the criterion for the execution of the above fourth loop, i.e., "if data sets previous and next to a data subset are both judged as noises, the segment of data set is also noise", the occurrence of the writing operation requires two essential conditions: firstly, only for data having a value of 0; and secondly, values adjacently before and after the value must be 1. Based on the two conditions, it is assumed that after values font or back are read by corresponding threads, if one of the values is modified, then values font or back must be 0, and values b and a are 1, or values a and c are 1. In other words, whether the heart data is font or back, value a must be 1. Obviously, this will not influence of the processing of value a by the thread, and the final result of value a will not be misjudged even if the heart data is read.

Therefore, heart data will not be read during the parallel execution of the fourth loop.

Figure 4:
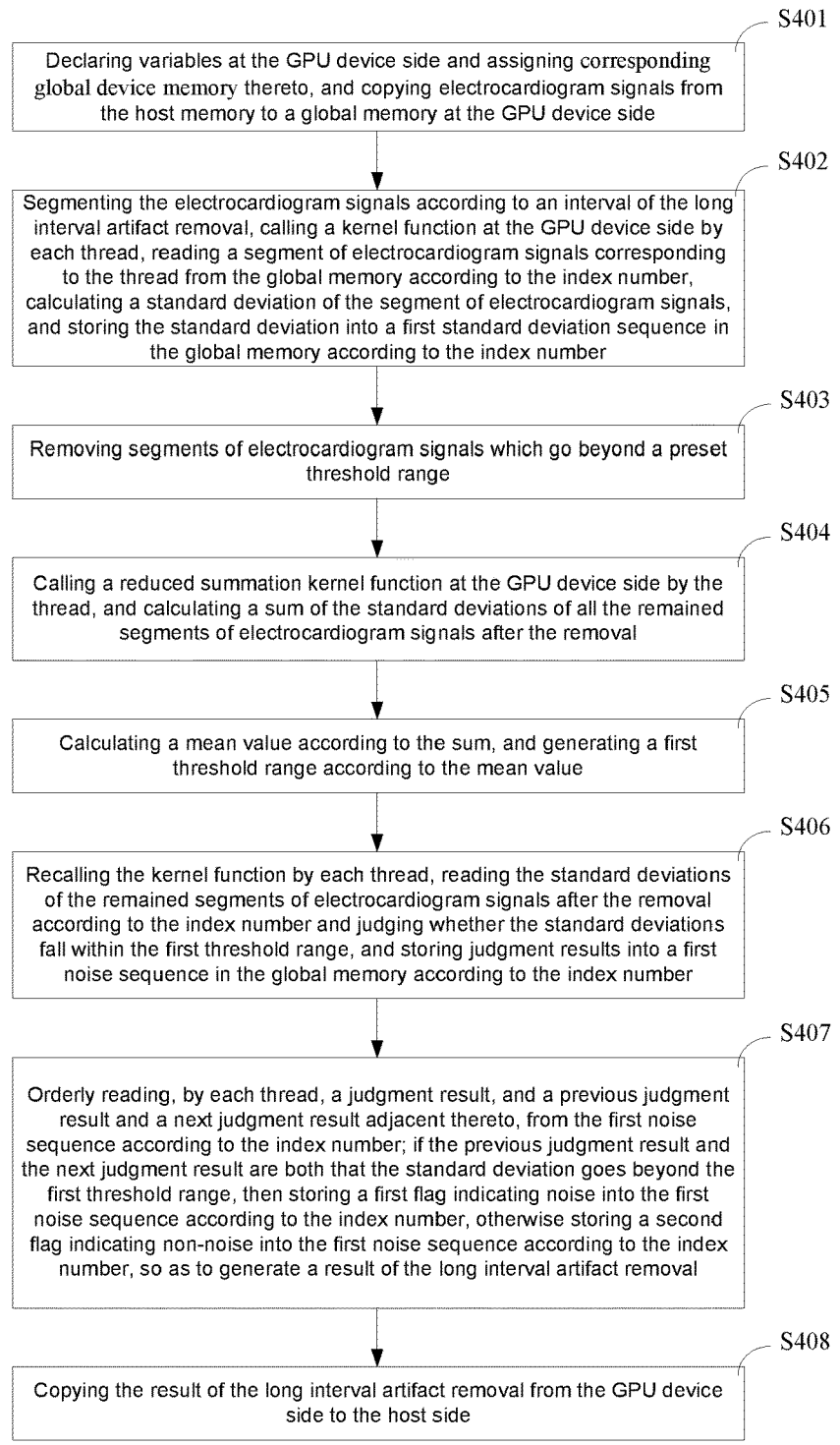
FIG. 4 is a flow diagram of a parallel execution algorithm of long interval artifact removal provided by an embodiment of the present disclosure.

FIG. 4 is a flow diagram of a parallel execution algorithm of long interval artifact removal provided by an embodiment of the present disclosure. As illustrated in FIG. 4, the long interval artifact removal is executed in parallel through a multiple the threads, comprising the steps of:

S401: declaring variables at the GPU device side and assigning corresponding global device memory thereto, and copying electrocardiogram signals from the host memory to a global memory at the GPU device side.

S402: segmenting the electrocardiogram signals according to an interval of the long interval artifact removal, calling a kernel function at the GPU device side by each thread, reading a segment of electrocardiogram signals corresponding to the thread from the global memory according to the index number, calculating a standard deviation of the segment of electrocardiogram signals, and storing the standard deviation into a first standard deviation sequence in the global memory according to the index number.

S403: removing segments of electrocardiogram signals which go beyond a preset threshold range.

S404: calling a reduced summation kernel function at the GPU device side by the thread, and calculating a sum of the standard deviations of all the remained segments of electrocardiogram signals after the removal.

S405: calculating a mean value according to the sum, and generating a first threshold range according to the mean value.

S406: recalling the kernel function by each thread, reading the standard deviations of the remained segments of electrocardiogram signals after the removal according to the index number and judging whether the standard deviations fall within the first threshold range, and storing judgment results into a first noise sequence in the global memory according to the index number.

S407: orderly reading, by each thread, a judgment result, and a previous judgment result and a next judgment result adjacent thereto, from the first noise sequence according to the index number; if the previous judgment result and the next judgment result are both that the standard deviation goes beyond the first threshold range, then storing a first flag indicating noise into the first noise sequence according to the index number, otherwise storing a second flag indicating non-noise into the first noise sequence according to the index number, so as to generate a result of the long interval artifact removal.

S408: copying the result of the long interval artifact removal from the GPU device side to the host side.

In step S401, the number of threads may be:

$$n = \frac{L}{f * T},$$

The number of the sample points of the electrocardiogram signals correspondingly processed by each thread may be f*T, where L is a sample point sequence length of the electrocardiogram signals copied from the host side, f is a sample frequency of the electrocardiogram signals, and T is an interval of the long interval artifact removal.

In step S402, the standard deviation may be calculated with the standard deviation calculation equation in step S303, i.e., the standard deviation:

$$M = \sqrt{\frac{\sum_{j=0}^{T*f-1}(p_j - m)^2}{T*f}}, m = \frac{\sum_{j=0}^{T*f-1}p_j}{T*f},$$

Where $p_j$ is the electrocardiogram signal at the $j^{th}$ sample point in the segment of electrocardiogram signals, j being an integer and j≥0, f is a sample frequency of the electrocardiogram signals, and T is an interval of the long interval artifact removal.

In step S403, the preset threshold range may be [0.5, 3]. In step S405, the upper limit and the lower limit of the first threshold range are 3 and 1/3.5 times of the mean value obtained in that step, respectively.

In step S407, the result of the long interval artifact removal may include electrocardiogram signal, noise/non-noise flag, and standard deviation data.

Figure 5:
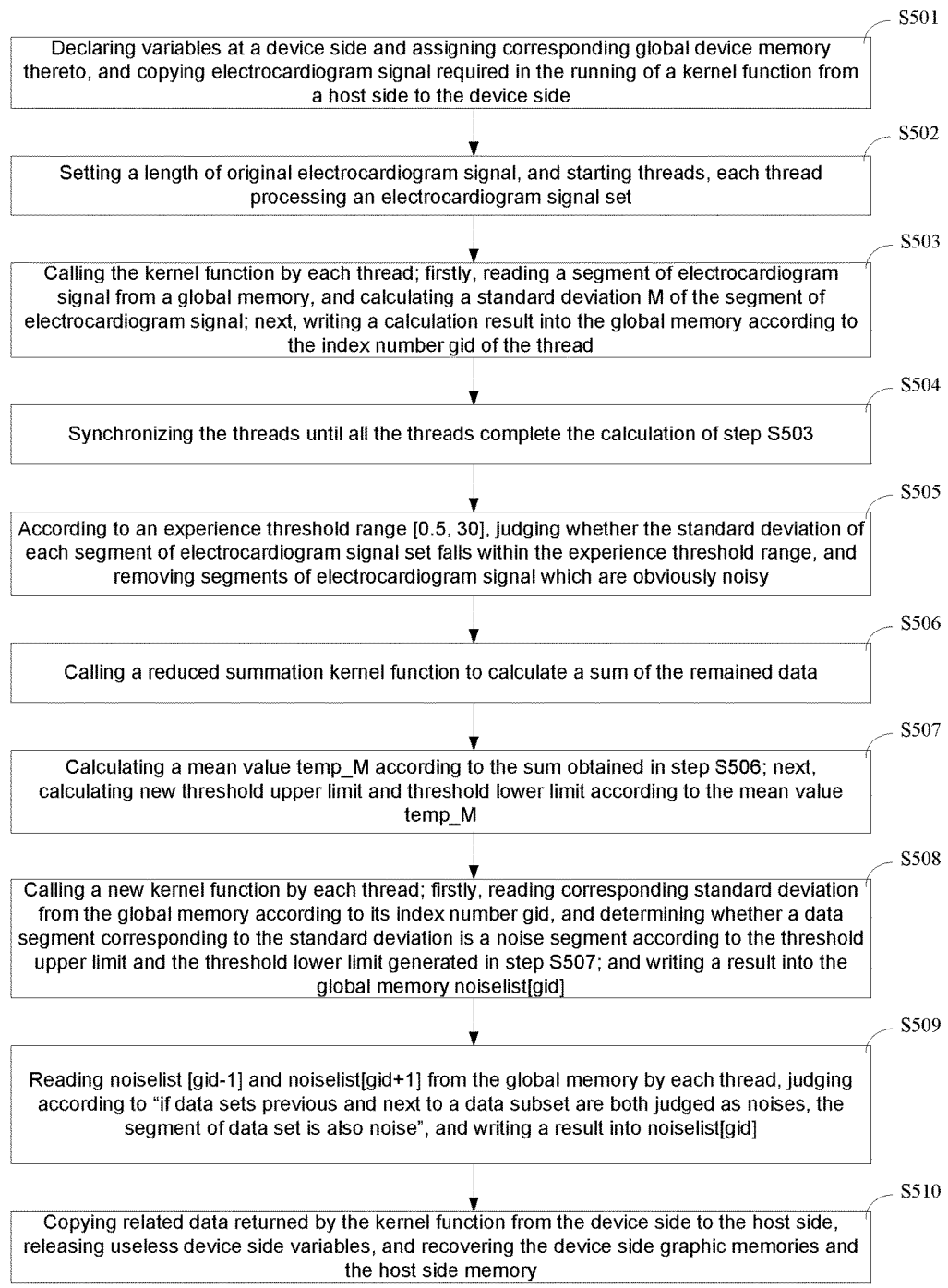
FIG. 5 is a flow diagram of a parallel execution algorithm of long interval artifact removal provided by an embodiment of the present disclosure.

FIG. 5 is a flow diagram of a parallel execution algorithm of long interval artifact removal provided by an embodiment of the present disclosure. As illustrated in FIG. 5, the parallel execution algorithm of the long interval artifact removal comprises the steps of:

S501: declaring variables at a device side and assigning corresponding global device memory thereto, and copying electrocardiogram signal required in the running of a kernel function from a host side to the device side.

S502: assuming that a length of the original electrocardiogram signal is L, and starting $$n = \frac{L}{f * T}$$

threads, i.e., each thread processes a data set containing f*T points of electrocardiogram signal.

S503: calling the kernel function by each thread; firstly, reading a segment of electrocardiogram signal from a global memory, and calculating a standard deviation M of the segment of electrocardiogram signal; next, writing a calculation result into the global memory according to the index number gid of the thread, i.e. st_d[gid]=M.

S504: synchronizing the threads until all the threads complete the calculation of step S503.

S505: according to an experience threshold range [0.5, 30], judging whether the standard deviation of each segment of electrocardiogram signal set falls within the experience threshold range, and removing segments of electrocardiogram signal which are obviously noisy.

S506: calling a reduced summation kernel function to calculate a sum of the remained data.

S507: calculating a mean value temp_M according to the sum obtained in step S506; next, calculating new threshold upper limit and threshold lower limit according to the mean value temp_M.

S508: calling a new kernel function by each thread; firstly, reading corresponding standard deviation from the global memory according to its index number gid, and determining whether a data segment corresponding to the standard deviation is a noise segment according to the threshold upper limit and the threshold lower limit generated in step S507; writing a result into the global memory noiselist[gid], and then performing the operation of thread synchronization.

S509: reading noiselist [gid−1] and noiselist[gid+1] from the global memory by each thread, judging according to "if data sets previous and next to a data subset are both judged as noises, the segment of data set is also noise", and writing a result into noiselist[gid].

S510: copying related data returned by the kernel function from the device side to the host side, releasing useless device side variables, and recovering the device side graphic memories and the host side memory.

In the embodiment of the present disclosure, through the parallel execution the long interval artifact removal algorithm at the GPU device side, the time consumption at the filtering process phase can be reduced obviously.

In one embodiment, the short interval artifact removal algorithm may be a serial algorithm. A short interval artifact removal may be performed for the electrocardiogram signals after the long interval artifact removal and the comb filter filtration. It mainly identifies the array noiselist according to the noise generated in the long interval artifact removal, and removes noise of a shorter interval $T_1$ from the data segment not identified as noise in the electrocardiogram signal, wherein the selection of the interval $T_1$ depends on the interval T of the long interval artifact removal, i.e., T may be a multiple of $T_1$. For example, the value of the interval T of the long interval artifact removal may be 5, and the value of the interval $T_1$ of the short interval artifact removal may be 1, which indicate a 5 s interval artifact and a is interval artifact. The noise sequence generated during the short interval artifact removal is denoted as noise[length], and the length of the array is length=ecgnum/$T_1$.

Figure 6:
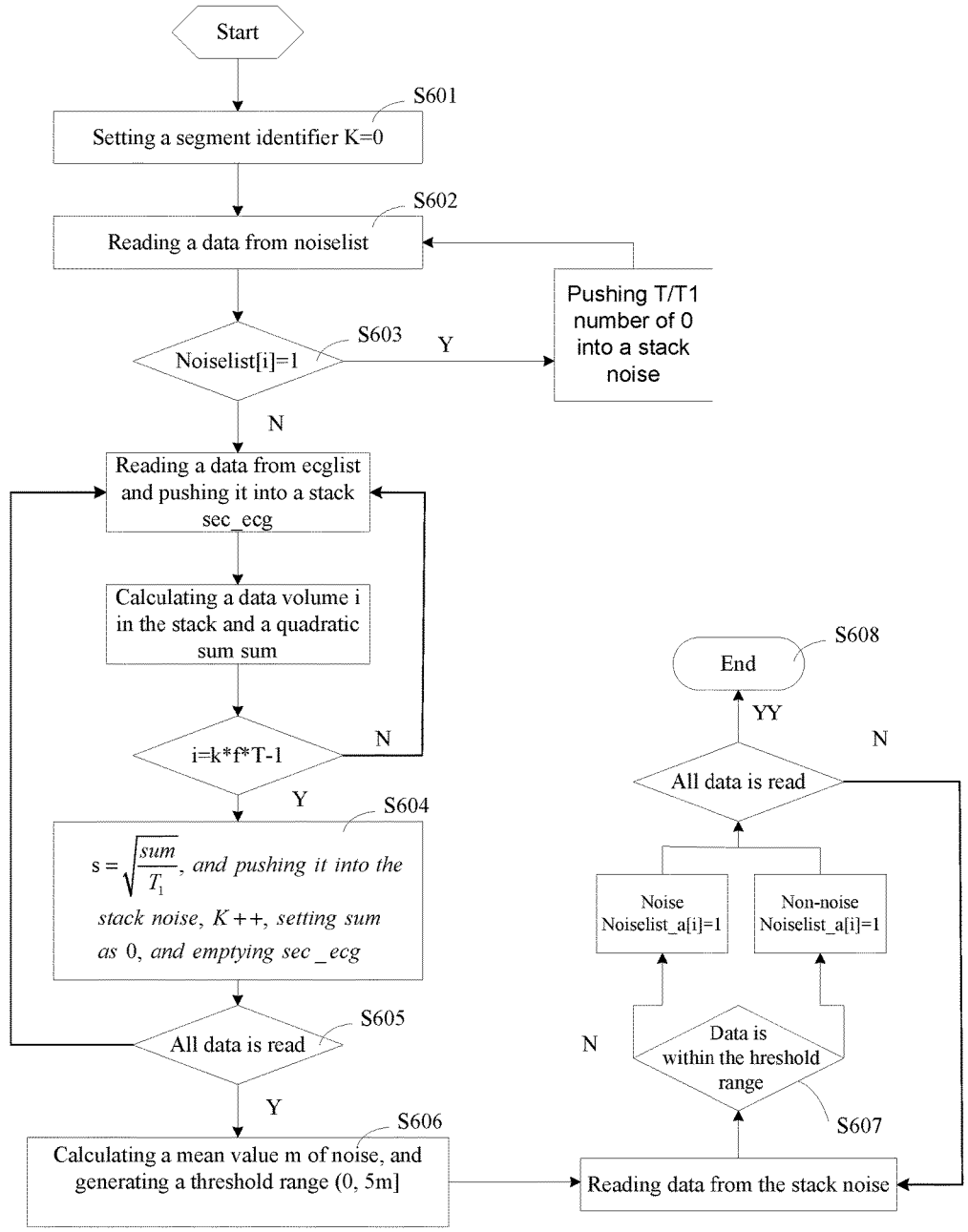
FIG. 6 is a flow diagram of a serial execution algorithm of short interval artifact removal provided by an embodiment of the present disclosure.

FIG. 6 is a flow diagram of a serial execution algorithm of short interval artifact removal provided by an embodiment of the present disclosure. As illustrated in FIG. 6, the serial execution algorithm of short interval artifact removal comprises the steps of:

S601: initializing environment variables.

S602: orderly reading data noiselist[i] from a noise sequence noiselist in the result of the long interval artifact removal.

S603: if the data noiselist[i]=1, it means that original electrocardiogram signal from ecglist[i*T*f] to ecglist[(i+1)*T*f−1] has been identified as a noise segment, then T/$T_1$ number of 0 are written into the array temp_noise in turn, i.e., a short interval artifact removal will not be performed for electrocardiogram signal corresponding to the noise segment.

S604: if the data noiselist[i]=0, orderly reading data started from a subscript i*T*f in the array ecglist corresponding to the data noiselist[i], calculating a value of the equation $S_{i,j}$, and writing the value of $S_{i,j}$ into temp_noise[i*T/T1+j]:

$$S_{i,j} = \sqrt{\frac{\sum_{n=i*(T/T_1)+j*f}^{i*(T/T_1)+(j+1)*T_1*f-1} p_n^2}{T_1}},$$

where $0 \leq j < \frac{T}{T_1}$,

T is a multiple of $T_1$, and $P_n$ is the value of the nth electrocardiogram signal.

S605: repeating steps S602, S603 and S604 until all the data in the noise sequence noiselist is read.

S606: calculating a mean value temp_S of all values greater than 0 in the newly obtained noise sequence temp_noise, thereby obtaining a new threshold range (0, 5*temp_S].

S607: judging according to the new threshold range obtained in step S606; if the data temp_noise[i] falls within the new threshold range, electrocardiogram signal corresponding to the data temp_noise[i] is not noise, i.e., noise[i]=0; otherwise the data is noise, i.e., noise[i]=1; returning the new noise sequence noise, repeating the step until all the data in the array temp_noise is read.

S608: ending the short interval artifact removal algorithm.

By analyzing the serial algorithm of the short interval artifact removal, the inventor finds that the short interval artifact removal algorithm has three large loops in total.

The first loop has a function of performing a shorter interval artifact removal for a non-noise data segment in the result of the long interval artifact removal, comprising: firstly, selecting a non-noise data segment from the noise sequence generated after the long interval artifact removal; and secondly, calculating in segments for the non-noise data segment at a shorter interval $T_1$. But when an improvement of parallel execution of the first loop is made, the serial order of the above two parts may be not observed. It is possible to firstly calculate in segments for all the original electrocardiogram signal at the interval $T_1$, i.e., to start thread resources in a corresponding number, each thread processing a data set sized as f*$T_1$, and write the calculation result into the graphic memory according to the index number of the thread; secondly, start the thread resources, wherein the number of the threads is equal to a length of the noise sequence in the result of the long interval artifact removal, and each thread is one-to-one corresponding to the data in the noise sequence obtained during the long interval artifact removal; and thirdly, correct the result of the previous calculation according to the data in the noise sequence.

The second loop has a function of calculating a mean value of all data greater than 0 in a result sequence calculated in the first loop. When a parallelization design is to be made, firstly data greater than 0 is serially selected and written into a new temporary array, then the reduced summation kernel function is called to calculate a sum of data in the temporary array, so as to obtain a mean value of all data greater than 0.

The third loop has a function of obtaining a new noise sequence according to the calculation results of the previous two loops. The parallel design thereof is to start thread resources of in a corresponding number, wherein each thread judges, according to its index number, whether the data corresponding to the index number is noise, and writes the result into the global graphic memory.

Figure 7:
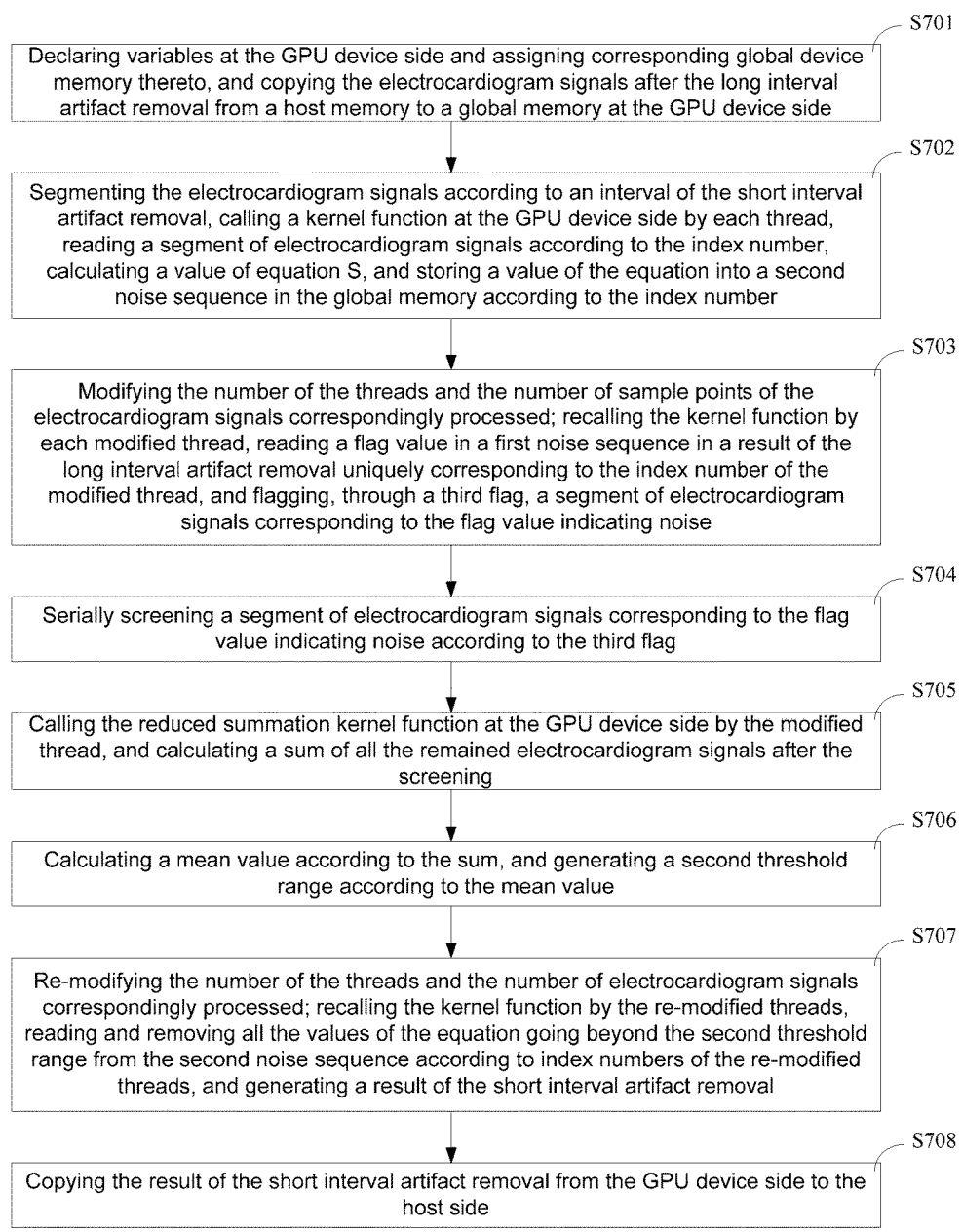
FIG. 7 is a flow diagram of a parallel execution algorithm of short interval artifact removal provided by an embodiment of the present disclosure.

FIG. 7 is a flow diagram of a parallel execution algorithm of short interval artifact removal provided by an embodiment of the present disclosure. As illustrated in FIG. 7, the parallel execution algorithm of short interval artifact removal comprises the steps of:

S701: declaring variables at the GPU device side and assigning corresponding global device memory thereto, and copying the electrocardiogram signals after the long interval artifact removal from a host memory to a global memory at the GPU device side.

S702: segmenting the electrocardiogram signals according to an interval $T_1$ of the short interval artifact removal, calling a kernel function at the GPU device side by each thread, reading a segment of electrocardiogram signals according to the index number, calculating a value of equation S, and storing a value of the equation into a second noise sequence in the global memory according to the index number, wherein equation S is:

$$s = \sqrt{\frac{sum}{T_1}},$$

where, sum is a quadratic sum of the electrocardiogram signals in all the segments of electrocardiogram signals.

S703: modifying the number of the threads and the number of sample points of the electrocardiogram signals correspondingly processed; recalling the kernel function by each modified thread, reading a flag value in a first noise sequence in a result of the long interval artifact removal uniquely corresponding to the index number of the modified thread, and flagging, through a third flag, a segment of electrocardiogram signals corresponding to the noise flag.

S704: serially screening a segment of electrocardiogram signals corresponding to the flag value indicating noise according to the third flag.

S705: calling the reduced summation kernel function at the GPU device side by the modified thread, and calculating a sum of all the remained electrocardiogram signals after the screening.

S706: calculating a mean value according to the sum, and generating a second threshold range according to the mean value.

S707: re-modifying the number of the threads and the number of electrocardiogram signals correspondingly processed; recalling the kernel function by the re-modified threads, reading and removing all the values of the equation going beyond the second threshold range from the second noise sequence according to index numbers of the re-modified threads, and generating a result of the short interval artifact removal.

S708: copying the result of the short interval artifact removal from the GPU device side to the host side.

In step S702, the electrocardiogram signals are segmented according to the interval of the short interval artifact removal firstly, and then a short interval artifact removal is performed in parallel for the electrocardiogram signals, which decreases the complexity of the parallel programs, and reduces the programming workload.

In step S702, the number of sample points of electrocardiogram signals processed by each thread may be $f*T_1$, and the number of the threads may be $$n = \frac{L}{f*T_1},$$

where L is a sample point sequence length of the electrocardiogram signals copied from the host side, and f is a sample frequency of the electrocardiogram signals. It may be set that ThreadsPerBlock threads are corresponding to a thread block, and the number of sample points of electrocardiogram signals corresponding to each thread block can be obtained from equation (1), i.e., DataPerBlock=$f*T*$ThreadsPerBlock The number of the thread blocks can be obtained from equation (2), i.e., BlockNum=($L$+DataPerBlock−1)/DataPerBlock In step S703, the number of the modified threads may be $$n = \frac{L}{f*T},$$

where L is a sample point sequence length of the electrocardiogram signals copied from the host side, f is a sample frequency of the electrocardiogram signals, and T is an interval of the long interval artifact removal. DataPerBlock1 modified threads may correspond to a thread block, and the number of the thread blocks can be calculated from equation (2):

BlockNum1=($L$1+DataPerBlock1−1)/DataPerBlock1,

Where in, L1 is the length of the first noise sequences from the long interval artifact removal.

In step S707, the number of the re-modified threads may be $$n = \frac{L}{f*T_1},$$

and each of the re-modified threads may correspondingly process one value of the equation. It may be set that ThreadsPerBlock2 number of re-modified threads correspond to one thread block, and the number of thread blocks can be calculated from equation (2):

BlockNum2=($n$+ThreadsPerBlock2−1)/ThreadsPerBlock2,

L is a sequence length of the sampled electrocardiogram signals copied from the host side. The result of the short interval artifact removal may comprise the electrocardiogram data, the noise/non-noise flag and the value of S.

In the embodiment of the present disclosure, the short interval artifact removal algorithm is a parallel execution algorithm, which can reduce the time consumption of the filtering phase and increase the electrocardiogram signal analysis speed.

In the embodiment of the present disclosure, the algorithm of the R-wave position extraction may be a mathematical morphological transform algorithm, and specifically, erosion and dilation operations in the mathematical morphological transform algorithm, i.e., an erosion operation is performed on the data at first, and then a dilation operation is performed on the data obtained after the erosion operation. The embodiment of the present disclosure may perform a dilation operation with the serial algorithm. During the erosion operation, the erosion window is set to have a size of 5, and a sliding rate of 1. Each time one data and four adjacently following data is read from the electrocardiogram signal ecglist. Next, erosion operations will be performed on the five read data at different degrees, and a minimum value is obtained and written into the temporary array f0. The dilation operation may be performed based on a temporary array f0 obtained after the erosion operation. During the dilation operation, the dilation window may also be set to have a size of 5, and a sliding rate of 1. Each time one data and four adjacently following data is read from the array f0. Next, dilation operations will be performed on the five read data at different degrees, and a maximum value is obtained and written into a temporary array f1.

Figure 8:
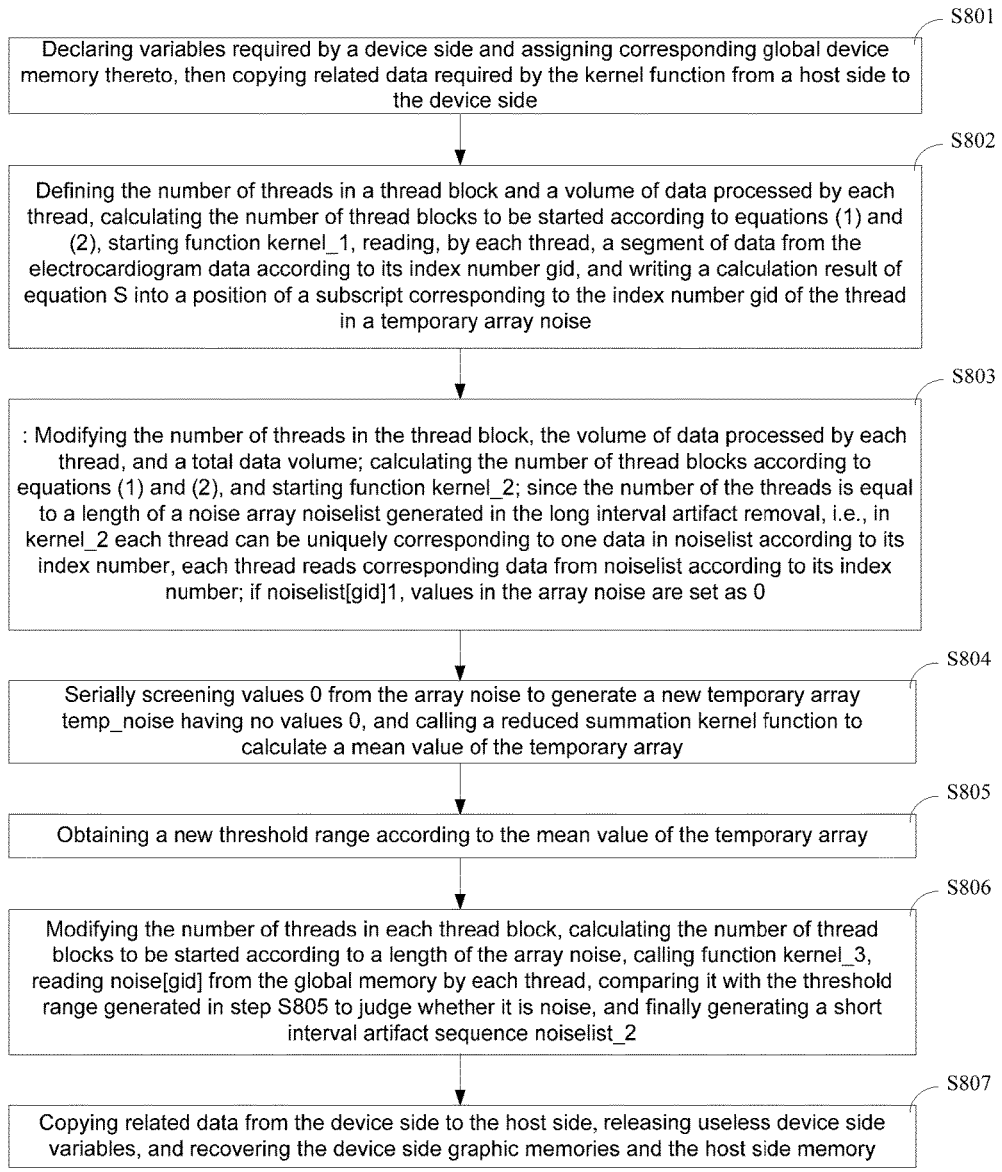
FIG. 8 is a flow diagram of a parallel execution algorithm of short interval artifact removal provided by another embodiment of the present disclosure.

FIG. 8 is a flow diagram of a parallel execution algorithm of short interval artifact removal provided by another embodiment of the present disclosure. As illustrated in FIG. 8, the parallel execution algorithm of the short interval artifact removal comprises the steps of:

S801: declaring variables required by a device side and assigning corresponding global device memory thereto, then copying related data required by the kernel function from a host side to the device side.

S802: defining the number ThreadsPerBlock of threads in a thread block and a volume DataPerThread=$f*T_1$ of data processed by each thread, calculating the number of thread blocks to be started according to equations (1) and (2), starting function kernel_1, reading, by each thread, data with subscripts from $gid*f*T_1$ to $(gid+1)*f*T_1-1$ from the electrocardiogram data according to its index number gid, and writing the calculation results into the positions of subscripts corresponding to the index number gid of the thread in the temporary array noise, where sum is a quadratic sum of data in the data set corresponding to the thread.

S803: modifying the number ThreadsPerBlock of threads in the thread block, the volume DataPerThread of data processed by each thread, and a total data volume $$n = \frac{L}{f*T}$$

(related variables have been defined in the long interval artifact removal, and herein n is a length of a noise array generated by the long interval artifact removal); calculating the number of thread blocks according to equations (1) and (2), and starting function kernel_2; since the number of the threads is equal to the length of the noise array noiselist generated in the long interval artifact removal, i.e., each thread in kernel_2 can be uniquely corresponding to one data in noiselist according to its index number, each thread in kernel_2 reads corresponding data from noiselist according to its index number; if noiselist[gid]=1, values with subscripts from gid*T to (gid+1)*T−1 in the array noise are set as 0.

S804: serially screening values 0 from the array noise to generate a new temporary array temp_noise having no values 0, and calling a reduced summation kernel function to calculate a mean value of the temporary array.

S805: obtaining a new threshold range according to the mean value of the temporary array.

S806: modifying the number ThreadsPerBlock of threads in each thread block, calculating the number BlockNum of thread blocks to be started according to the length $$n = \frac{L}{f*T_1}$$

of the array noise, calling function kernel_3, reading noise [gid] from the global memory by each thread, comparing it with the threshold range generated in step S805 to judge whether it is noise, and finally generating a short interval artifact sequence noiselist_2.

S807: copying related data from the device side to the host side, releasing useless device side variables, and recovering the device side graphic memories and the host side memory.

Figure 9:
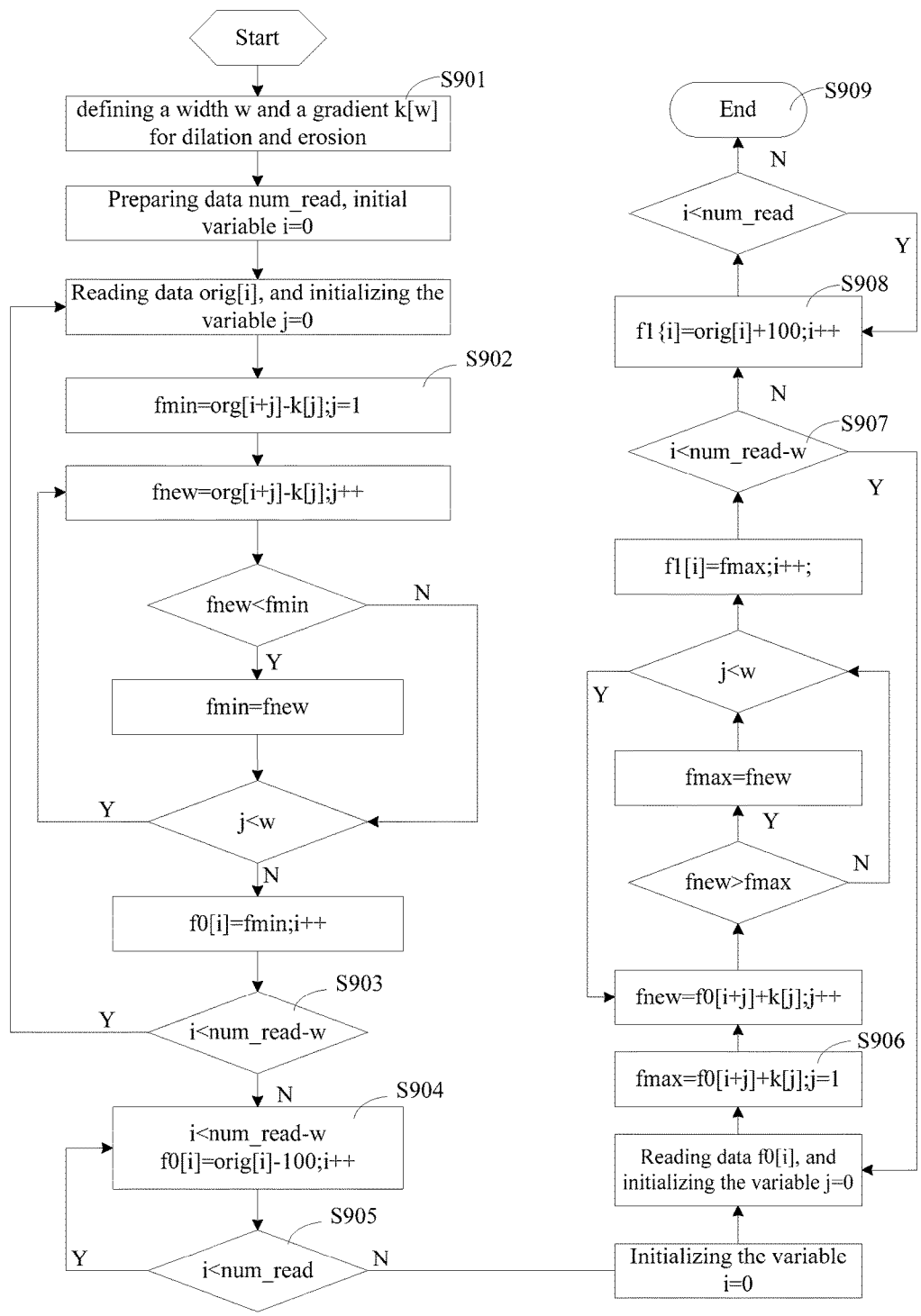
FIG. 9 is a flow diagram of a serial execution algorithm of R-wave position extraction provided by an embodiment of the present disclosure.

In one embodiment, the algorithm of the R-wave position extraction adopts a serial algorithm. FIG. 9 is a flow diagram of a serial execution algorithm of R-wave position extraction provided by an embodiment of the present disclosure. As illustrated in FIG. 9, the serial execution algorithm of the R-wave position extraction comprises the steps of:

S901: defining windows of a dilation operation and an erosion operation to have a size w=5 and a gradient k[w]={0, 50, 100, 50, 0}.

S902: orderly reading one electrocardiogram signal ecglist[i] and four following electrocardiogram signal ecglist [i+1], ecglist[i+2], ecglist[i+3] and ecglist[i+4] from electrocardiogram signal ecglist, performing erosion operations with corresponding gradients in step S901 at different degrees to obtain a minimum value, and writing the minimum value into an array f0[i].

S903: repeating step S902 until the array ecglist has only four data left.

S904: performing an erosion operation at the greatest degree on the last four electrocardiogram signal ecglist [num_read-w+1], ecglist[num_read-w+2], ecglist [num_read-w+3] and ecglist[num_read-w+4] in the electrocardiogram signal ecglist, and writing the result of the erosion operation into f0[num_read-w+1], f0[num_read-w+2], f0[num_read-w+3] and f0[num_read-w+4].

S905: ending the erosion operation.

S906: performing a dilation operation on a result set array f0 obtained in the erosion operation: orderly reading one data f0[i] and following data f0[i+1], f0[i+2], f0[i+3] and f0[i+4] from the array f0; and performing dilation operations at respective degrees with corresponding gradients in step S901 respectively to obtain a maximum value, and writing the maximum value into an array f1[i].

S907: repeating step S906 until the array f0 has the last four data left.

S908: performing a dilation operation at the greatest degree on the last four data left in step S907, respectively, i.e., adding ecglist[num_read-w+1], ecglist[num_read-w+2], ecglist[num_read-w+3] and ecglist[num_read-w+4] with 100, respectively, and writing into f1[num_read-w+1], f1[num_read-w+2], f1[num_read-w+3] and f1[num_read-w+4].

S909: ending the dilation operation.

Finally, differences between the data ecglist[i] and the data f1[i] are calculated, and a mean value of all the differences is calculated and written into a global graphic memory s1[i]. The calculation result is returned and the mathematical morphological transform algorithm is ended.

By analyzing the serial execution algorithm of the R-wave position extraction, the inventor finds that in the serial execution algorithm, the mathematical morphological dilation operation and erosion operation on all electrocardiogram data are not performed at one time, but in several batches. Each time a certain volume (num_read) of electrocardiogram data is read from the filtering-processed electrocardiogram data, and put in a dilation operation and an erosion operation. Corresponding logical judgments are made according to the operation results to extract all the R-wave positions in the segment of electrocardiogram data.

A manner of "one on one" is adopted to make a parallelization improvement to the algorithm of the R-wave position extraction.

Each time the kernel function is called to perform the dilation operation and the erosion operation, thread resources in the same volume of the data are started, so that each thread finds an unique electrocardiogram data point according to its index number. Next, the dilation and erosion operations are performed on the data and four adjacently following data, and the calculation results are written into the global graphic memory according to the index number of the thread. During the parallel execution, the inventor further finds that the program calls the kernel function for several times, and writes data required by the present kernel function from the CPU side memory into the GPU side graphic memory before each time of calling, thus the program execution efficiency is seriously affected by the frequent data transmissions between the CPU and the GUP. In the following embodiment, the inventor makes a further optimization.

Figure 10:
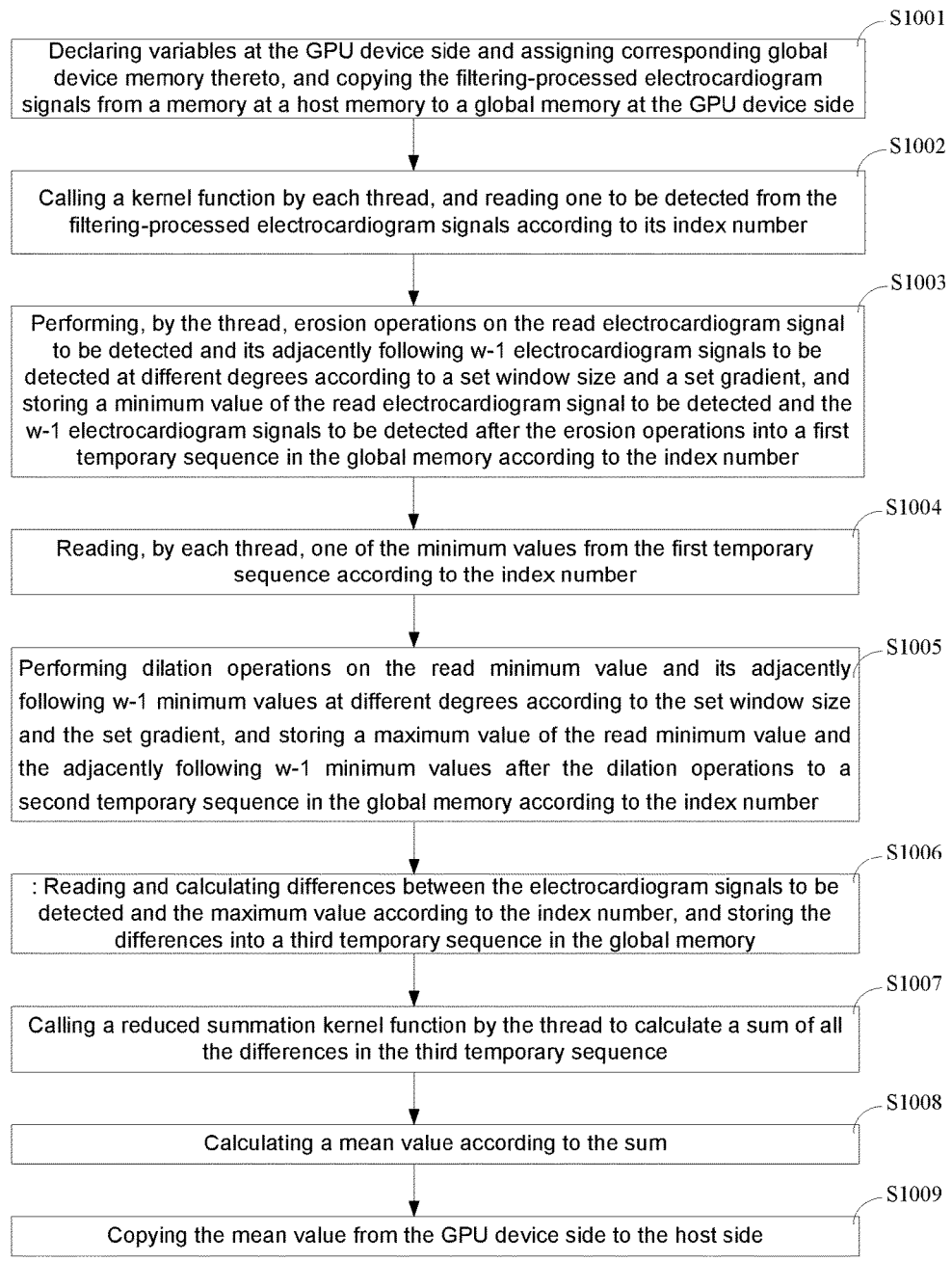
FIG. 10 is a flow diagram of a parallel execution algorithm of R-wave position extraction provided by an embodiment of the present disclosure.

FIG. 10 is a flow diagram of a parallel execution algorithm of R-wave position extraction provided by an embodiment of the present disclosure. As illustrated in FIG. 10, the parallel execution algorithm of the R-wave position extraction comprises the steps of:

S1001: declaring variables at the GPU device side and assigning corresponding global device memory thereto, and copying the filtering-processed electrocardiogram signals from a memory at a host memory to a global memory at the GPU device side.

S1002: calling a kernel function by each thread, and reading one to be detected from the filtering-processed electrocardiogram signals according to its index number.

S1003: performing, by the thread, erosion operations on the read electrocardiogram signal to be detected and its adjacently following w−1 electrocardiogram signals to be detected at different degrees according to a set window size w and a set gradient, and storing a minimum value of the read electrocardiogram signal to be detected and the w−1 electrocardiogram signals to be detected after the erosion operations into a first temporary sequence in the global memory according to the index number, where w is an integer and w≥2.

S1004: reading, by each thread, one of the minimum values from the first temporary sequence according to the index number.

S1005: performing dilation operations on the read minimum value and its adjacently following w−1 minimum values at different degrees according to the set window size and the set gradient, and storing a maximum value of the read minimum value and the adjacently following w−1 minimum values after the dilation operations to a second temporary sequence in the global memory according to the index number.

S1006: reading and calculating differences between the electrocardiogram signals to be detected and the maximum value according to the index number, and storing the differences into a third temporary sequence in the global memory.

S1007: calling a reduced summation kernel function by the thread to calculate a sum of all the differences in the third temporary sequence.

S1008: calculating a mean value according to the sum.

S1009: copying the mean value from the GPU device side to the host side.

In the embodiment of the present disclosure, the parallel execution algorithm of the R-wave position extraction writes all filtering-processed electrocardiogram data into the GPU graphic memory, and set a flag bit to mark the read position, so that when being executed, the kernel function reads the presently required electrocardiogram data from the graphic memory according to the flag bit while updating the flag bit. The method transfers the data preparation from the CPU to the GPU, so that data is written from the CPU memory to the GPU graphic memory for only one time, thereby greatly reducing the time consumption of the data transmission.

In the embodiment of the present disclosure, after the mean value is obtained in step S1008, the R-wave position can be calculated at the host side according to the mean value.

In step S1003, the minimum value of the read electrocardiogram signal to be detected and the w−1 electrocardiogram signals to be detected after the erosion operations may also be stored in to a register. In step S1004, one minimum value is read from the register, and then w−1 minimum values adjacent thereto are read from the global memory.

As a result, since data is simultaneously read from the global memory and the register, the speed of the R-wave position extraction can be further increased.

In step S1003, the set window size and the set gradient may be different set values. For example, the set window size is w=5, and the set gradient is k[w]={0, 50, 100, 50, 0}.

In step S1002, the number of threads may be equal to the sample point sequence length L3 of the electrocardiogram signal copied from the host side, and it may be set that ThreadsPerBlock3 number of threads correspond to one thread block, and the number of the thread blocks may be:

BlockNum3=(L3+ThreadsPerBlock3−1)/ThreadsPerBlock3.

Thus the complexity of the parallel algorithm can be decreased.

Figure 11:
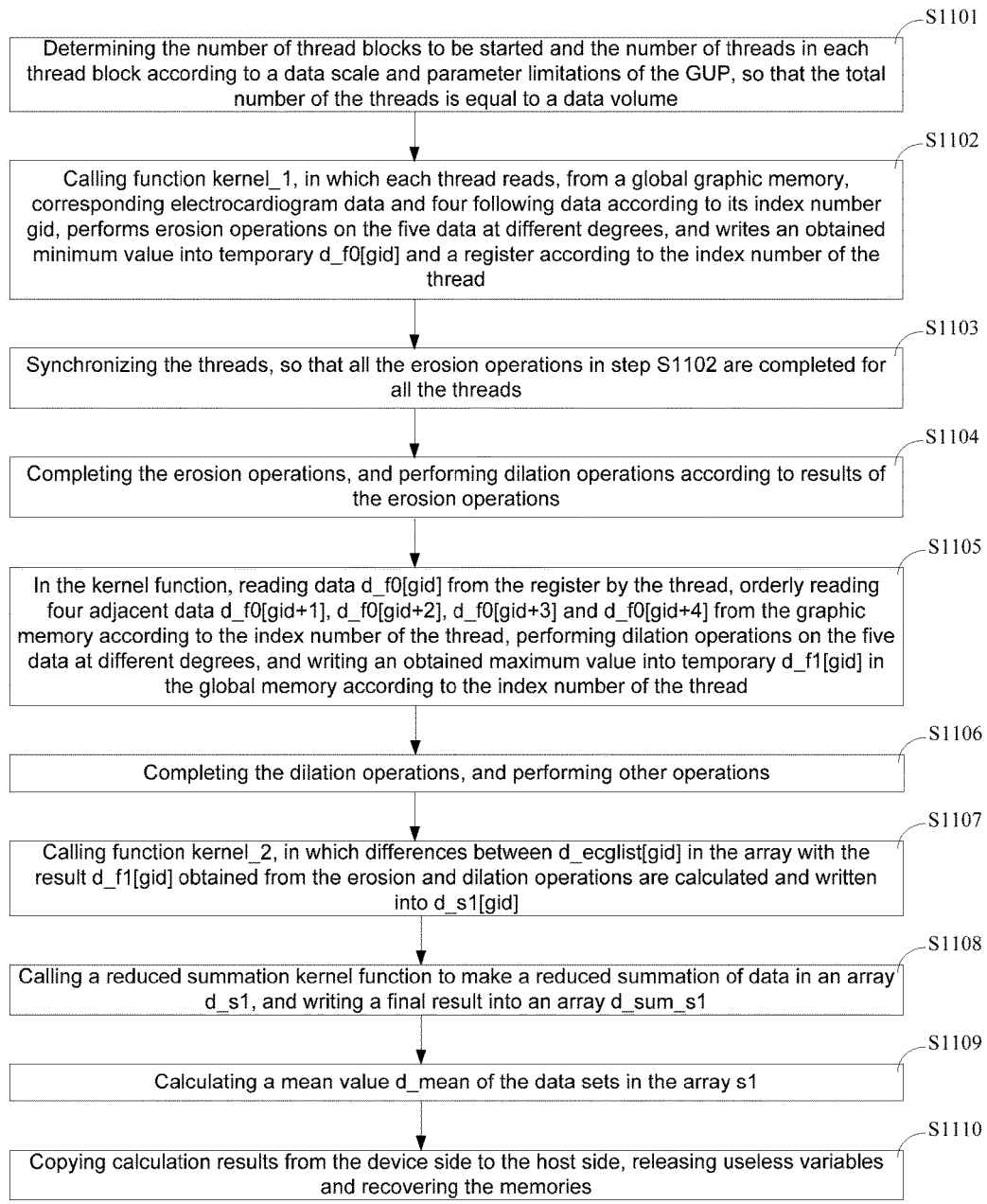
FIG. 11 is a flow diagram of a parallel execution algorithm of R-wave position extraction provided by another embodiment of the present disclosure.

FIG. 11 is a flow diagram of a parallel execution algorithm of R-wave position extraction provided by another embodiment of the present disclosure. As illustrated in FIG. 11, the parallel execution algorithm of the R-wave position extraction comprises the steps of:

S1101: determining the number BlockNum of thread blocks to be started and the number threadPerBlock of threads in each thread block according to a data scale and parameter limitations of the GUP, so that the total number of the threads is equal to a data volume.

S1102: calling function kernel_1, in which each thread reads, from a global graphic memory, corresponding electrocardiogram data and four following data according to its index number gid, performing erosion operations on the five data at different degrees, and writing an obtained minimum value into temporary d_f0[gid] and a register according to the index number of the thread.

S1103: synchronizing the threads, so that all the erosion operations in step S1102 are completed for all the threads.

S1104: completing the erosion operations, and performing dilation operations according to results of the erosion operations.

S1105: in the kernel function, reading data d_f0[gid] from the register by the thread, orderly reading four adjacent data d_f0[gid+1], d_f0[gid+2], d_f0[gid+3] and d_f0[gid+4] from the graphic memory according to the index number of the thread, performing dilation operations on the five data at different degrees, and writing an obtained maximum value into temporary d_f1[gid] in the global memory according to the index number of the thread.

S1106: completing the dilation operations, and performing other operations.

S1107: calling function kernel_2, in which differences between d_ecglist[gid] in the array with the result d_f1[gid] obtained from the erosion and dilation operations are calculated and written into d_s1[gid].

S1108: calling a reduced summation kernel function to make a reduced summation of data in an array d_s1, and writing a final result into an array d_sum_s1.

S1109: calculating a mean value d mean of the data sets in the array s1.

S1110: copying calculation results from the device side to the host side, releasing useless variables and recovering the memories.

In the embodiment of the present disclosure, the QRS complex start and end positions extraction can be achieved by a method of peak group determination. Wave peaks and wave troughs near R-wave are found, and edge positions of the QRS complex are determined according to a preset threshold. The characteristic parameters required for the QRS complex start position extraction depend on the R-wave position extraction. The calculation of the width of the QRS complex mainly relies on two data sets: i.e., a data set QRS_startlist and a data set QRS_endlist. The data set QRS_startlist stores start points of the QRS complex, and the data set QRS_endlist stores end points of the QRS complex, thus the width of the QRS complex is a difference between them.

Figure 12:
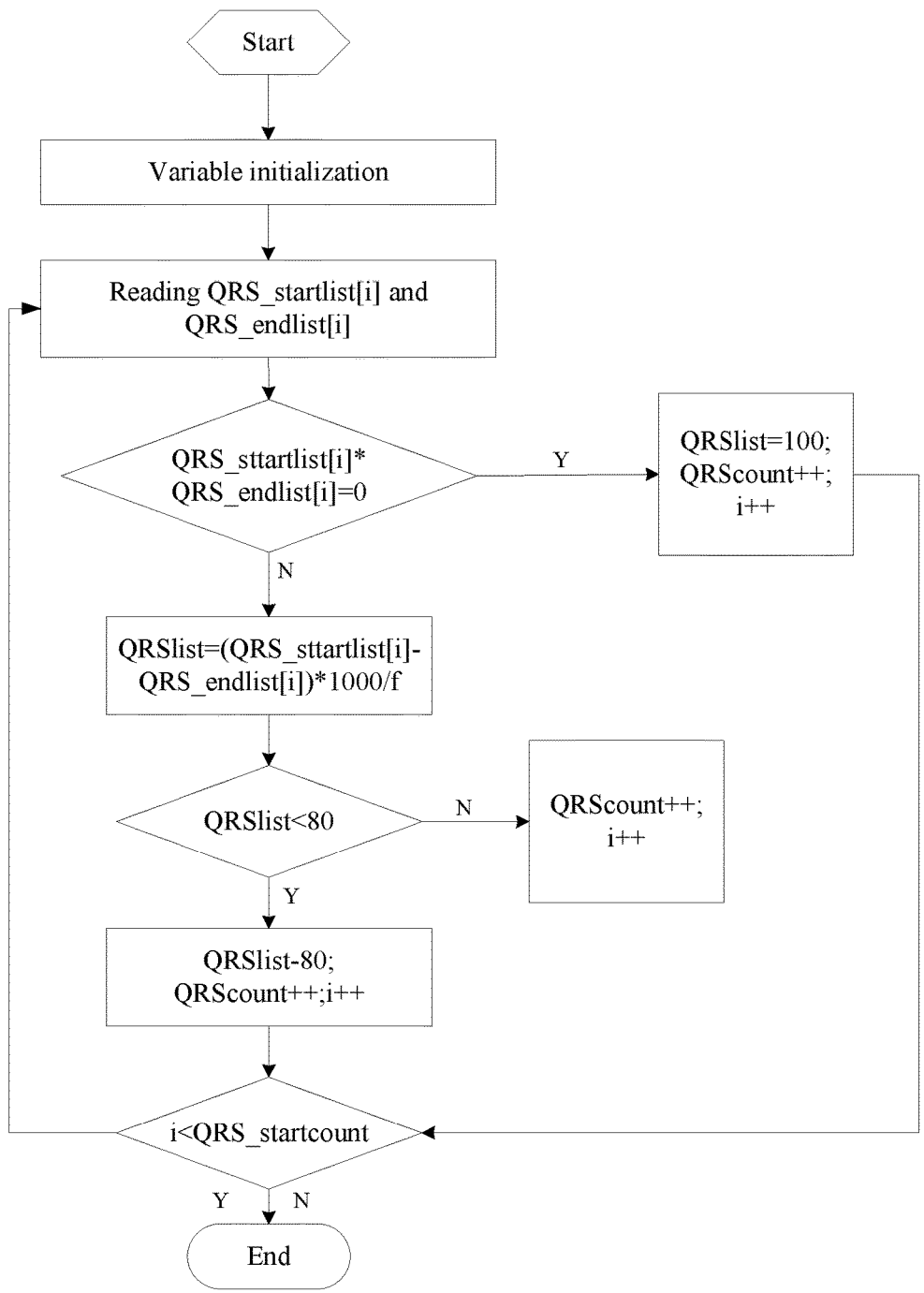
FIG. 12 is a flow diagram of a serial execution algorithm of QRS complex width extraction provided by an embodiment of the present disclosure.

In one embodiment, the QRS complex width extraction is performed with a serial algorithm. FIG. 12 is a flow diagram of a serial execution algorithm of QRS complex width extraction provided by an embodiment of the present disclosure. As illustrated in FIG. 12, during the execution of the serial algorithm, a start position QRS_startlist[i] and an end position QRS_endlist[i] of the QRS complex are orderly read from a start point data set QRS_startlist and an end point data set QRS_endlist of the QRS complex, so as to calculate a difference QRSlist between the start position QRS_startlist[i] and the end position QRS_endlist[i], and determine whether the difference QRSlist shall be recorded according to a preset threshold 80.

In another embodiment, the QRS complex width extraction is performed with a parallel algorithm. Corresponding number of thread resources are started according to the length of the data set QRS_startlist and the length of the data set QRS_endlist, then each thread reads corresponding data from the data set QRS_startlist and the data set QRS_endlist according to its index number gid respectively and calculates a difference between them so as to obtain a width of corresponding QRS complex, and finally writes the width of the QRS complex into the global graphic memory according to its index number.

Figure 13:
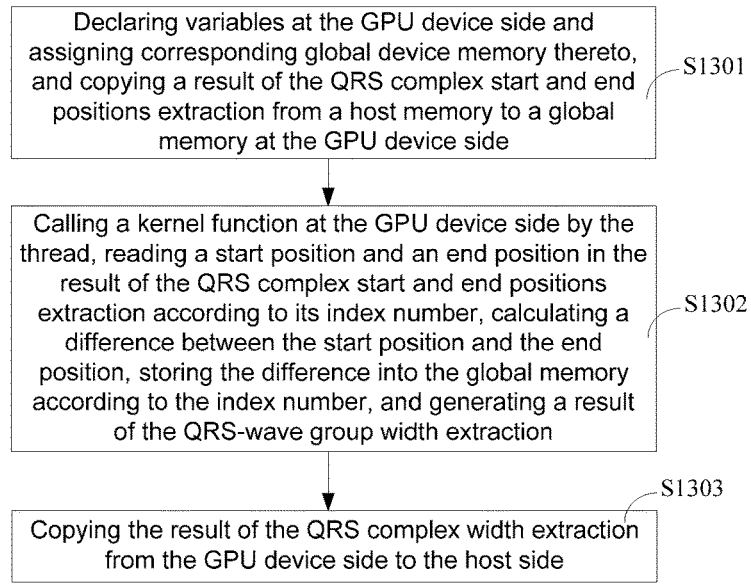
FIG. 13 is a flow diagram of a parallel execution algorithm of QRS complex width extraction provided by an embodiment of the present disclosure.

FIG. 13 is a flow diagram of a parallel execution algorithm of QRS complex width extraction provided by an embodiment of the present disclosure. As illustrated in FIG. 13, the parallel execution algorithm of the QRS complex width extraction comprises the steps of:

S1301: declaring variables at the GPU device side and assigning corresponding global device memory thereto, and copying a result of the QRS complex start and end positions extraction from a host memory to a global memory at the GPU device side.

S1302: calling a kernel function at the GPU device side by the thread, reading a start position and an end position in the result of the QRS complex start and end positions extraction according to its index number, calculating a difference between the start position and the end position, storing the difference into the global memory according to the index number, and generating a result of the QRS complex width extraction.

S1303: copying the result of the QRS complex width extraction from the GPU device side to the host side.

In the embodiment of the present disclosure, the start position and the end position of the QRS complex can be obtained at the host side according to a method of peak group determination, so that the steps which are not easy for parallel execution are serially executed at the host side, thereby reducing the time consumption of copying data between the CPU and the GUP.

In step S1302, the number blocknum of thread blocks to be started and the number threadsPerBlock of threads in each thread block can be determined according to a data scale and parameter limitations of the GUP. The total number of the started threads may be blocknum*threadPerBlock. The thread reads corresponding start position data QRS_startlist[gid] and end position data QRS_endlist[gid] from the QRS complex start position data set QRS_startlist and the QRS complex end position data set QRS_endlist in the global memory respectively according to its index number gid, so as to calculate the width of the QRS complex, and then writes a calculation result into QRSlist[gid] according to its index number.

In the embodiment of the present disclosure, the used start position and end position of the QRS complex can be calculated at the host side.

In the embodiment of the present disclosure, the serial algorithm of the abnormal waveform classification may comprise four steps:

Step 1: determining 13 or multiple types of cardiac beats one by one;

Step 2: determining data segments seriously polluted by noise, heart beats with too small amplitudes, atrial premature beats and ventricular premature beats.

Step 3: determining dropped beats and stopped beats.

Step 4: adopting a template comparison method for all abnormal waves.

By analyzing the four steps of the above abnormal waveform classification, the inventor finds that the fourth step of template comparison consumes more than 95% time of the whole algorithm, thus a parallel speedup can be made for the most time-consuming part. The template comparison method is to establish a QRS template near each abnormal cardiac beat. The core part of the template comparison method consumes the maximum time. The core part is to generate an identifier sequence according to an RR interval RRlist, wherein the identifiers includes three values of −1, 0 and 1.

Figure 14:
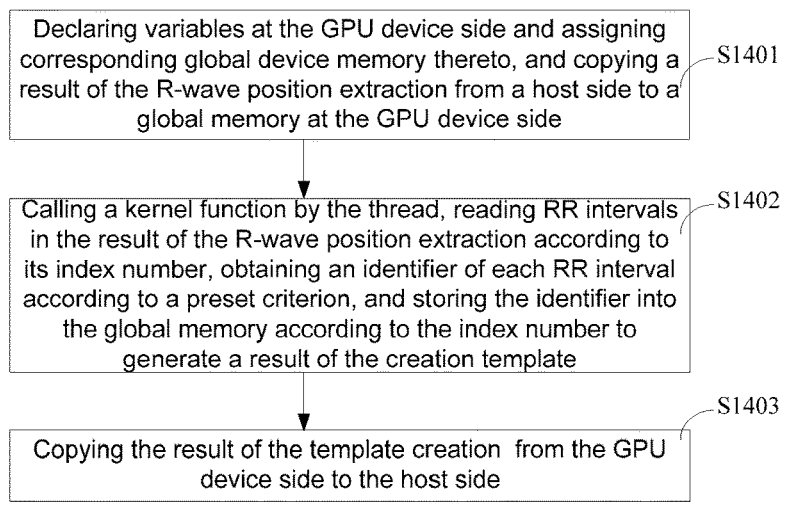
FIG. 14 is a flow diagram of a parallel execution algorithm of a creation template provided by an embodiment of the present disclosure.

FIG. 14 is a flow diagram of a parallel execution algorithm of a creation template provided by an embodiment of the present disclosure. As illustrated in FIG. 14, the parallel execution algorithm of the creation template comprises the steps of:

S1401: declaring variables at the GPU device side and assigning corresponding global device memory thereto, and copying a result of the R-wave position extraction from a host memory to a global memory at the GPU device side.

S1402: calling a kernel function by the thread, reading RR intervals in the result of the R-wave position extraction according to its index number, obtaining an identifier of each RR interval according to a preset criterion, and storing the identifier into the global memory according to the index number to generate a result of the creation template.

S1403: copying the result of the template creation from the GPU device side to the host side.

In the embodiment of the present disclosure, the RR interval can be calculated at the host side from the result of the R-wave position extraction.

In step S1402, the preset criterion may comprise:

(1) if the i+1th RR interval RRlist[i+1] adjacent to the ith RR interval RRlist[i] goes beyond the range (0.6*RRlist[i], 1.5*RRlist[i]), the identifier of the RR interval data RRlist[i] is −1, where i is an integer and i≥0.

(2) if the RR interval RRlist[i+1] falls within the range (0.6*RRlist[i], 1.5*RRlist[i]) and the RR interval RRlist[i] goes beyond the range (0.8*RRmean, 1.3*RRmean), the identifier of the RR interval RRlist[i] is 0, where RRmean is a mean value of all the RR intervals.

(3) if the RR interval RRlist[i+1] falls within the range (0.6*RRlist[i], 1.5*RRlist[i]) and the RR interval RRlist[i] falls within the range (0.8*RRmean, 1.3*RRmean), the identifier of the RR interval RRlist[i] is 1.

In step S1402, number blocknum of thread blocks to be started and the number threadsPerBlock of threads in each thread block can be determined according to a data scale and parameter limitations of the GUP. The number of the started threads may be blocknum*threadPerBlock. Each thread reads corresponding RR interval data from the global graphic memory according to its index number, so as to obtain corresponding identifier according to the three criteria, and then writes a result into d_FLAGRlist[gid] according to its index number.

The template is created near the abnormal cardiac beat, i.e., when an abnormal cardiac beat is found, a template shall be created by calling a template creation function. Thus when there are many abnormal waves, much time will be consumed at that phase. In the embodiment of the present disclosure, an identifier sequence needs not to be regenerated each time a template is created. Thus by optimizing the generation of the identifier sequence and the template creation, the embodiment of the present disclosure can obviously reduce the time consumption of the abnormal waveform classification.

The parallel electrocardiogram signal analysis method of the embodiment of the present disclosure always keeps an accurate rate consistent with that of the serial electrocardiogram signal analysis method. The serial and parallel algorithms are tested for multiple times using the 24 h long-term electrocardiogram signal, and then a mean value thereof is taken to obtain electrocardiogram signals to analyze the speed-up ratio of each phase, as shown in Table 1.

TABLE 1

Sequential Running Time, Parallel Running Time, and Corresponding Speed-Up Ratios

|  | Sequential running time (ms) | Parallel running time (ms) | Speed-up ratio |
| --- | --- | --- | --- |
| Long interval artifact removal algorithm | 392 | 54 | 7.3 |
| Short interval artifact removal algorithm | 261 | 44 | 5.9 |
| Mathematical morphological transform algorithm | 1685 | 160 | 10.5 |

TABLE 1-continued

Sequential Running Time, Parallel Running Time, and Corresponding Speed-Up Ratios

|  | Sequential running time (ms) | Parallel running time (ms) | Speed-up ratio |
| --- | --- | --- | --- |
| QRS complex width detection algorithm | 7 | 6.8 | 1.0 |
| classification and detection | 1562 | 30.2 | 48.5 |

As can be seen from the data comparison in Table 1, at the filtering phase of the electrocardiogram signal analysis, the mean time consumption of the sequential running of the long interval artifact removal algorithm is 392 ms, and the mean running time after the parallel design and optimization is 54 ms, and the obtained speed-up ratio is 7.3; the mean running time of the short interval artifact removal algorithm is 261 ms, the mean running time after the parallel design and optimization is 44 ms, and the obtained speed-up ratio is 5.9; at the QRS complex detection phase of the electrocardiogram signal, the sequential running speed of mathematical morphological dilation operation and erosion operation is 1685 ms, while the mean running time after the parallel design and optimization is 160 ms, and the speed-up ratio is 10.5; the sequential running time of the QRS complex width calculation is 7 ms, the mean running time after the parallel speedup is 6.8 ms, and the speed-up ratio is close to 1; the mean value of the sequential running time of the arrhythmia waveform classification algorithm is 1562 ms, the running speed after the parallel speedup is 30.2, and the obtained speed-up ratio is 48.5.

During comparisons between the running time before and after the parallel speedup of various algorithms, it can be found that when the sequential running time of the algorithm increases, the speed-up ratio obtained by the parallel speedup rises, and when the sequential running time of the algorithm decreases, the speed-up ratio obtained by the parallel speedup reduce.

The parallel algorithm of the embodiment of the present disclosure is analyzed and tested for multiple times by using the electrocardiogram signal sample sets having different time durations, so as to obtain a mean analysis time, as shown in Table 2. As can be seen from Table 2, when the number of abnormal waveforms increases, the analysis time gets longer, thus the parallel electrocardiogram signal analysis method of the embodiment of the present disclosure is well adaptive to electrocardiogram signal files having different time durations. Each analysis time can be kept within 2 s. The mean analysis time of the electrocardiogram signal having a time duration of 24 h is 1.9 s. Assuming that the electrocardiogram signal uploaded to the family health cloud platform is uniformly distributed to respective periods in every day, then one "CPU+GPU" server can analyze the 24 h long-term electrocardiogram signal in real-time for a volume of 44920 one day. Thus, the requirement of rapid analyses of 300 thousands of 24 h long-term electrocardiogram signal every day can be satisfied just by deploying an algorithm server cluster composed of seven "CPU+GPU" servers on the family health cloud platform.

TABLE 2

Analysis Time of Electrocardiogram Data Having Different Time Durations

| | Electrocardiogram time duration | | | | | | | |
|---|---|---|---|---|---|---|---|---|
| | 1 | 2 | 4 | 8 | 12 | 16 | 20 | 24 |
| File size | 0.5 | 1 | 2.1 | 4.1 | 6.2 | 8.3 | 10.3 | 12.4 |
| Analysis time | 105 | 183 | 345 | 676 | 1023 | 1364 | 1644 | 1932 |

The present disclosure accelerates the analysis of long-term electrocardiogram data by using a "GPU+CPU" heterogeneous parallel system, i.e., firstly using a GPU (Graphic Processing Unit) acceleration technology to parallelize the parallelizable part and the time-consuming part in the sequential electrocardiogram analysis algorithm, and accelerate the electrocardiogram analysis at the instruction level; then deploying GPU servers loaded with the parallel electrocardiogram analysis algorithm on the family health cloud platform to meet the requirement of the family health cloud service platform at present.

The present disclosure provides a computer readable storage medium containing computer readable instructions which when being executed, cause a processor to at least:

performing a filtering process of electrocardiogram signals through a long interval artifact removal and a short interval artifact removal;

performing a QRS detection of the filtering-processed electrocardiogram signals through an R-wave position extraction, a QRS complex start and end positions extraction and a QRS complex width extraction; and performing an abnormal waveform classification of the QRS-detected electrocardiogram signals through template creation;

wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data.

Figure 15:
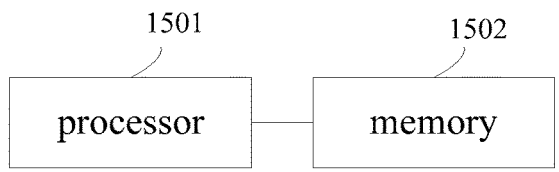
FIG. 15 is a structure diagram of a device in the embodiment of the present disclosure.

The present disclosure provides a device, as illustrated in FIG. 15, comprising:

a processor 1501; and a memory 1502 containing computer readable instructions which when being executed, cause the processor to at least:

performing a filtering process of electrocardiogram signals through a long interval artifact removal and a short interval artifact removal;

performing a QRS detection of the filtering-processed electrocardiogram signals through an R-wave position extraction, a QRS complex start and end positions extraction and a QRS complex width extraction; and performing an abnormal waveform classification of the QRS-detected electrocardiogram signals through template creation;

wherein at least one of the long interval artifact removal, the short interval artifact removal, the R-wave position extraction, the QRS complex width extraction and the creation template is performed by a multiple threads at a GPU device side in parallel, any thread being read through its unique index number to process corresponding data.

By executing one or more steps of the electrocardiogram signal analysis process at the GPU in parallel, the GPU-based parallel electrocardiogram analysis method of the embodiment of the present disclosure obviously increases the analysis speed of the electrocardiogram signal.

A person skilled in the art shall appreciate that the embodiments of the present disclosure can provide a method, a system, or a computer program product. Therefore, the present disclosure can employ the embodiments of complete hardware, complete software or a combination of hardware and software. In addition, the present disclosure can employ the form of a computer program product implementable in one or more computer readable storage mediums (including but not limited to disk memory, CD-ROM, optical memory, etc.) containing computer readable program codes.

The present disclosure is described with reference to the flowcharts and/or block diagrams of the method, the device (system) and the computer program product of the embodiments of the present disclosure. It shall be appreciated that each flow and/or block in the flowcharts and/or the block diagrams and combinations of the flows and/or blocks in the flowcharts and/or the block diagrams can be realized by computer program instructions. Those computer program instructions can be provided to the processor of a general purpose computer, a dedicated computer, an embedded processing machine or other programmable data processing device to generate a machine, so that instructions executed by the processor of the computer or other programmable data processing device generate means for realizing the functions specified in one or more flows and/or one or more blocks of the block diagram.

Those computer program instructions can also be stored in a computer readable memory which can guide the computer or other programmable data processing device to work in a specific mode, so that the instructions stored in the computer readable memory generates a manufactured article including instruction to realize the functions specified in one or more flows of the flowchart and/or one or more blocks of the block diagram.

Those computer program instructions can also be loaded to the computer or other programmable data processing device, so that a series of operation steps are performed in the computer or other programmable data processing device to achieve a processing realized by the computer, therefore the instructions executed in the computer or other programmable data processing device provide steps for realizing the functions specified in one or more flows of the flowchart and/or one or more blocks of the block diagram.

The above embodiments further describe the objects in detail, technical solutions and beneficial effects of the present disclosure. It shall be appreciated that those are just specific embodiments of the present disclosure, rather than limitations to the protection scope of the present disclosure. Any amendment, equivalent replacement, improvement, etc. made within the spirit and principle of the present disclosure shall fall within the protection scope of the present disclosure.

The invention claimed is:

1. A GPU-based parallel electrocardiogram signal analysis method, comprising:

performing a filtering process of electrocardiogram signals through a long interval artifact removal and a short interval artifact removal; through parallel execution, the long interval artifact removal is performed at the GPU device side and the short interval artifact removal is performed for the electrocardiogram signals after the long interval artifact removal and comb filter filtration;

performing a QRS detection of the filtering-processed electrocardiogram signals through an R-wave position extraction, a QRS complex start and end positions extraction and a QRS complex width extraction; and performing an abnormal waveform classification of the QRS complex through template creation;

wherein at least one of the long interval artifact removal, the short interval artifact removal, the R-wave position extraction, the QRS complex width extraction of QRS complex and the template creation is performed by multiple threads at a GPU device side in parallel; the thread being read through its unique index number, and processing its corresponding data.

2. The GPU-based parallel electrocardiogram signal analysis method according to claim 1, wherein the long interval artifact removal is executed by the multiple threads in parallel, comprising:

declaring variables at the GPU device side and assigning corresponding global device memory thereto, and copying the electrocardiogram signals from a host memory to a global memory at the GPU device;

segmenting the electrocardiogram signals according to an interval of the long interval artifact removal, calling a kernel function at host side by a process, reading a segment of electrocardiogram signals corresponding to the thread from the global memory according to the index number, calculating a standard deviation of the segment of electrocardiogram signals, and storing the standard deviation into a first standard deviation sequence in the global memory according to the index number;

removing segments of electrocardiogram signals which go beyond a preset threshold range;

calling a reduced summation kernel function at the GPU device side by the thread, and calculating a sum of the standard deviations of all the remained segments of electrocardiogram signals after the removal;

calculating a mean value according to the sum, and generating a first threshold range according to the mean value;

recalling the kernel function by each thread, reading the standard deviations of the remained segments of electrocardiogram signals after the removal according to the index number and judging whether the standard deviations fall within the first threshold range, and storing judgment results into a first noise sequence in the global memory according to the index number;

orderly reading, by each thread, a judgment result and a previous judgment result and a next judgment result adjacent thereto, from the first noise sequence according to the index number; if the previous judgment result and the next judgment result are both that the standard deviation goes beyond the first threshold range, then storing a first flag indicating noise into the first noise sequence according to the index number, otherwise storing a second flag indicating non-noise into the first noise sequence according to the index number, so as to generate a result of the long interval artifact removal; copying the result of the long interval artifact removal from the GPU device side to the host side.

3. The GPU-based parallel electrocardiogram signal analysis method according to claim 2, wherein the number of the threads is $$n = \frac{L}{f*T},$$

and the number of sample points of the electrocardiogram signal correspondingly processed by each thread is f*T, where L is a sample point sequence length of the electrocardiogram signals copied from the host side, f is the sample frequency of the electrocardiogram signals, and T is the interval of the long interval artifact removal.

4. The GPU-based parallel electrocardiogram signal analysis method according to claim 2, wherein the standard deviation is $$M = \sqrt{\frac{\sum_{j=0}^{T*f-1}(p_j - m)^2}{T*f}}, \text{ where } m = \frac{\sum_{j=0}^{T*f-1} p_j}{T*f},$$

$p_j$ is the electrocardiogram signal at the $j^{th}$ sample point in the segment of electrocardiogram signals, j being an integer and j≥0, f is a sample frequency of the electrocardiogram signals, and T is an interval of the long interval artifact removal.

5. The GPU-based parallel electrocardiogram signal analysis method according to claim 2, wherein an upper limit of the first threshold range is 3 times of the mean value, and a lower limit of the first threshold range is 1/3.5 times of the mean value.

6. The GPU-based parallel electrocardiogram signal analysis method according to claim 2, wherein the preset threshold range is [0.5, 3].

7. The GPU-based parallel electrocardiogram signal analysis method according to claim 1, wherein the short interval artifact removal is executed by multiple threads in parallel, comprising:

declaring variables at the GPU device side and assigning corresponding global device memory thereto, and copying the electrocardiogram signals after the long interval artifact removal from a host memory to a global memory at the GPU device side;

segmenting the electrocardiogram signals according to an interval $T_1$ of the short interval artifact removal, calling a kernel function at host side by a process, reading a segment of electrocardiogram signals according to the index number, calculating a value of equation $$s = \sqrt{\frac{\text{sum}}{T_1}},$$

and storing a value of the equation into a second noise sequence in the global memory according to the index number, wherein sum is a quadratic sum of the electrocardiogram signals in all the segments of electrocardiogram signals;

modifying the number of the threads and the number of sample points of the electrocardiogram signals correspondingly processed; recalling the kernel function by each modified thread, reading a flag value in a first noise sequence in a result of the long interval artifact removal uniquely corresponding to the index number of the modified thread, and flagging, through a third flag, a segment of electrocardiogram signals corresponding to the flag value indicating noise;

serially screening a segment of electrocardiogram signals corresponding to the flag value indicating noise according to the third flag;

calling a reduced summation kernel function at host side by the modified thread, and calculating a sum of all the remained electrocardiogram signals after the screening;

calculating a mean value according to the sum, and generating a second threshold range according to the mean value;

re-modifying the number of the threads and the number of the electrocardiogram signals correspondingly processed; recalling the kernel function by the re-modified threads, reading and removing all the values of the equation going beyond the second threshold range from the second noise sequence according to index numbers of the re-modified threads, and generating a result of the short interval artifact removal;

copying the result of the short interval artifact removal from the GPU device side to the host side.

8. The GPU-based parallel electrocardiogram signal analysis method according to claim 7, further comprising:
the number of sample points of the electrocardiogram signals processed by each thread is $f*T_1$, and the number of the threads is $$n = \frac{L}{f*T_1},$$

where L is a sample point sequence length of the electrocardiogram signals copied from the host side, and f is a sample frequency of the electrocardiogram signals;

setting that Threads Per Block threads are corresponding to a thread block, and the number of sample points of the electrocardiogram signals corresponding to each thread block is DataPerBlock=f*T*ThreadsPerBlock, and the number of the thread blocks is BlockNum=(L+DataPerBlock−1)/DataPerBlock.

9. The GPU-based parallel electrocardiogram signal analysis method according to claim 7, further comprising:
the number of the modified threads is $$n = \frac{L}{f*T},$$

where L is a sample point sequence length of the electrocardiogram signals copied from the host side, f is a sample frequency of the electrocardiogram signals, and T is an interval of the long interval artifact removal; DataPerBlock1 modified threads are corresponding to a thread block, and the number of the thread blocks is BlockNum1=(L1+DataPerBlock1−1)/DataPerBlock1, where L1 is a length of the first noise sequences of all the results of the long interval artifact removal.

10. The GPU-based parallel electrocardiogram signal analysis method according to claim 6, further comprising:
the number of the re-modified threads is $$n = \frac{L}{f*T_1},$$

and correspondingly processing one value of the equation by each re-modified thread; setting that ThreadsPerBlock2 re-modified threads are corresponding to a thread block, and the number of the thread blocks is BlockNum2=(n+ThreadsPerBlock2−1)/ThreadsPerBlock2, L is a sample point sequence length of the electrocardiogram signals copied from the host side.

11. The GPU-based parallel electrocardiogram signal analysis method according to claim 1, wherein the R-wave position detection is executed by the multiple threads in parallel, comprising:

declaring variables at the GPU device side and assigning corresponding global device memory thereto, and copying the filtering-processed electrocardiogram signals from a memory at a host memory to a global memory at the GPU device side;

calling a kernel function by each thread, and reading one to be detected from the filtering-processed electrocardiogram signals according to its index number;

performing, by the thread, erosion operations on the read electrocardiogram signal to be detected and its adjacently following w−1 electrocardiogram signals to be detected at different degrees according to a set window size w and a set gradient, and storing a minimum value of the read electrocardiogram signal to be detected and the w−1 electrocardiogram signals to be detected after the erosion operations into a first temporary sequence in the global memory according to the index number, where w is an integer and w≥2;

reading, by each thread, one of the minimum values from the first temporary sequence according to the index number;

performing dilation operations on the read minimum value and its adjacently following w−1 minimum values at different degrees according to the set window size and the set gradient, and storing a maximum value of the read minimum value and the adjacently following w−1 minimum values after the dilation operations to a second temporary sequence in the global memory according to the index number;

reading and calculating differences between the electrocardiogram signals to be detected and the maximum value according to the index number, and storing the differences into a third temporary sequence in the global memory;

calling a reduced summation kernel function by the thread to calculate a sum of all the differences in the third temporary sequence;

calculating a mean value according to the sum;

copying the mean value from the GPU device side to the host side.

12. The GPU-based parallel electrocardiogram signal analysis method according to claim 11, further comprising:

storing the minimum value of the read electrocardiogram signal to be detected and the w−1 electrocardiogram signals to be detected after the erosion operations into a register;

reading the minimum value from the register, and reading the w−1 minimum values from the global memory.

13. The GPU-based parallel electrocardiogram signal analysis method according to claim 11, wherein the set window size is w=5, and the set gradient is k[w]={0, 50, 100, 50, 0}.

14. The GPU-based parallel electrocardiogram signal analysis method according to claim 11, wherein the number of the threads is equal to a sample point sequence length L3 of the electrocardiogram signals copied from the host side; setting that ThreadsPerBlock3 threads are corresponding to a thread block, and the number of the thread blocks is BlockNum3=(L3+ThreadsPerBlock3−1)/ThreadsPerBlock3.

15. The GPU-based parallel electrocardiogram signal analysis method according to claim 1, wherein the extracting width of QRS complex is executed by the multiple threads in parallel, comprising:

declaring variables at the GPU device side and assigning corresponding global memory thereto, and copying a result of the QRS complex start and end positions extraction from a host memory to a global memory at the GPU device side;

calling a kernel function at the host side by the thread, reading a start position and an end position in the result of the QRS complex start and end positions extraction according to its index number, calculating a difference between the start position and the end position, storing the difference into the global memory according to the index number, and generating a result of the QRS complex width extraction;

copying the result of the QRS complex width extraction from the GPU device side to the host side.

16. The GPU-based parallel electrocardiogram signal analysis method according to claim 15, wherein the start position and the end position of the QRS complex are obtained at the host side according to a method of peak group determination.

17. The GPU-based parallel electrocardiogram signal analysis method according to claim 1, wherein the creation template is executed by the multiple threads in parallel, comprising:

declaring variables at the GPU device side and assigning corresponding global device memory thereto, and copying a result of the R-wave position extraction from a host memory to a global memory at the GPU device side;

calling a kernel function by the thread, reading RR intervals in the result of the R-wave position extraction according to its index number, obtaining an identifier of each RR interval according to a preset criterion, and storing the identifier into the global memory according to the index number to generate a result of the creation template;

copying the result of the creation template from the GPU device side to the host side.

18. The GPU-based parallel electrocardiogram signal analysis method according to claim 17, wherein the preset criterion comprises:

if an (i+1)th RR interval RRlist[i+1] adjacent to an ith RR interval RRlist[i] goes beyond a range (0.6*RRlist[i], 1.5*RRlist[i]), an identifier of the RR interval data RRlist[i] is −1, where i is an integer and i≥0;

if the RR interval RRlist[i+1] falls within the range (0.6*RRlist[i], 1.5*RRlist[i]) and the RR interval RRlist[i] goes beyond a range (0.8*RRmean, 1.3*RRmean), the identifier of the RR interval RRlist[i] is 0, where RRmean is a mean value of all the RR intervals; and if the RR interval RRlist[i+1] falls within the range (0.6*RRlist[i], 1.5*RRlist[i]) and the RR interval RRlist[i] falls within the range (0.8*RRmean, 1.3*RRmean), the identifier of the RR interval RRlist[i] is 1.

19. A device, comprising:

a processor; and a memory containing computer readable instructions which when being executed, cause the processor to at least:

perform a filtering process of electrocardiogram signals through a long interval artifact removal and a short interval artifact removal; through parallel execution, the long interval artifact removal is performed at the GPU device side and the short interval artifact removal is performed for the electrocardiogram signals after the long interval artifact removal and comb filter filtration;

perform a QRS detection of the filtering-processed electrocardiogram signals through an R-wave position extraction, a QRS complex start and end positions extraction and a QRS complex width extraction; and perform an abnormal waveform classification of the QRS-detected electrocardiogram signals through template creation;

wherein at least one of the long interval artifact removal, the short interval artifact removal, the R-wave position extraction, the QRS complex width extraction and the template creation is performed by a multiple threads at a GPU device side in parallel, any thread being read through its unique index number to process corresponding data.

20. A computer readable storage medium containing computer readable instructions which when being executed, cause a processor to at least:

perform a filtering process of electrocardiogram signals through a long interval artifact removal and a short interval artifact removal; through parallel execution, the long interval artifact removal is performed at the GPU device side and the short interval artifact removal is performed for the electrocardiogram signals after the long interval artifact removal and comb filter filtration;

perform a QRS detection of the filtering-processed electrocardiogram signals through an R-wave position extraction, a QRS complex start and end positions extraction and a QRS complex width extraction; and perform an abnormal waveform classification of the QRS-detected electrocardiogram signals through template creation;

wherein at least one of the long interval artifact removal, the short interval artifact removal, the R-wave position extraction, the QRS complex width extraction and the template creation is performed by a multiple threads at a GPU device side in parallel, any thread being read through its unique index number to process corresponding data.

* * * * *